(12) United States Patent
Ma et al.

(10) Patent No.: US 7,930,105 B2
(45) Date of Patent: Apr. 19, 2011

(54) GRADING OF BREAST CANCER

(75) Inventors: Xiao-Jun Ma, San Diego, CA (US);
Dennis C. Sgroi, Winchester, MA (US);
Mark G. Erlander, Encinitas, CA (US)

(73) Assignees: bioTheranostics, Inc., San Diego, CA (US); The General Hospital Corporation, Boston, MA (US)

( * ) Notice: Subject to any disclaimer, the term of this patent is extended or adjusted under 35 U.S.C. 154(b) by 501 days.

(21) Appl. No.: 11/946,835

(22) Filed: Nov. 28, 2007

(65) Prior Publication Data

US 2009/0092973 A1    Apr. 9, 2009

Related U.S. Application Data

(63) Continuation of application No. 10/211,015, filed on Aug. 1, 2002, now abandoned, which is a continuation-in-part of application No. 10/028,018, filed on Dec. 21, 2001, now abandoned.

(51) Int. Cl.
*G06F 7/00* (2006.01)

(52) U.S. Cl. .............. 702/19; 702/20; 703/11; 707/700; 435/6; 536/24.5

(58) Field of Classification Search ..................... None
See application file for complete search history.

(56) References Cited

OTHER PUBLICATIONS

Ma et al. PNAS USA vol. 100, No. 10, pp. 5974-5979, 2003.*

* cited by examiner

*Primary Examiner* — Mary K Zeman
(74) *Attorney, Agent, or Firm* — Patentique PLLC

(57) ABSTRACT

Methods and compositions for the identification of breast cancer grade signatures are provided. The signature profiles are identified based upon multiple sampling of reference breast tissue samples from independent cases of breast cancer and provide a reliable set of molecular criteria for identification of cells as being in one or more particular stages and/or grades of breast cancer.

20 Claims, 5 Drawing Sheets

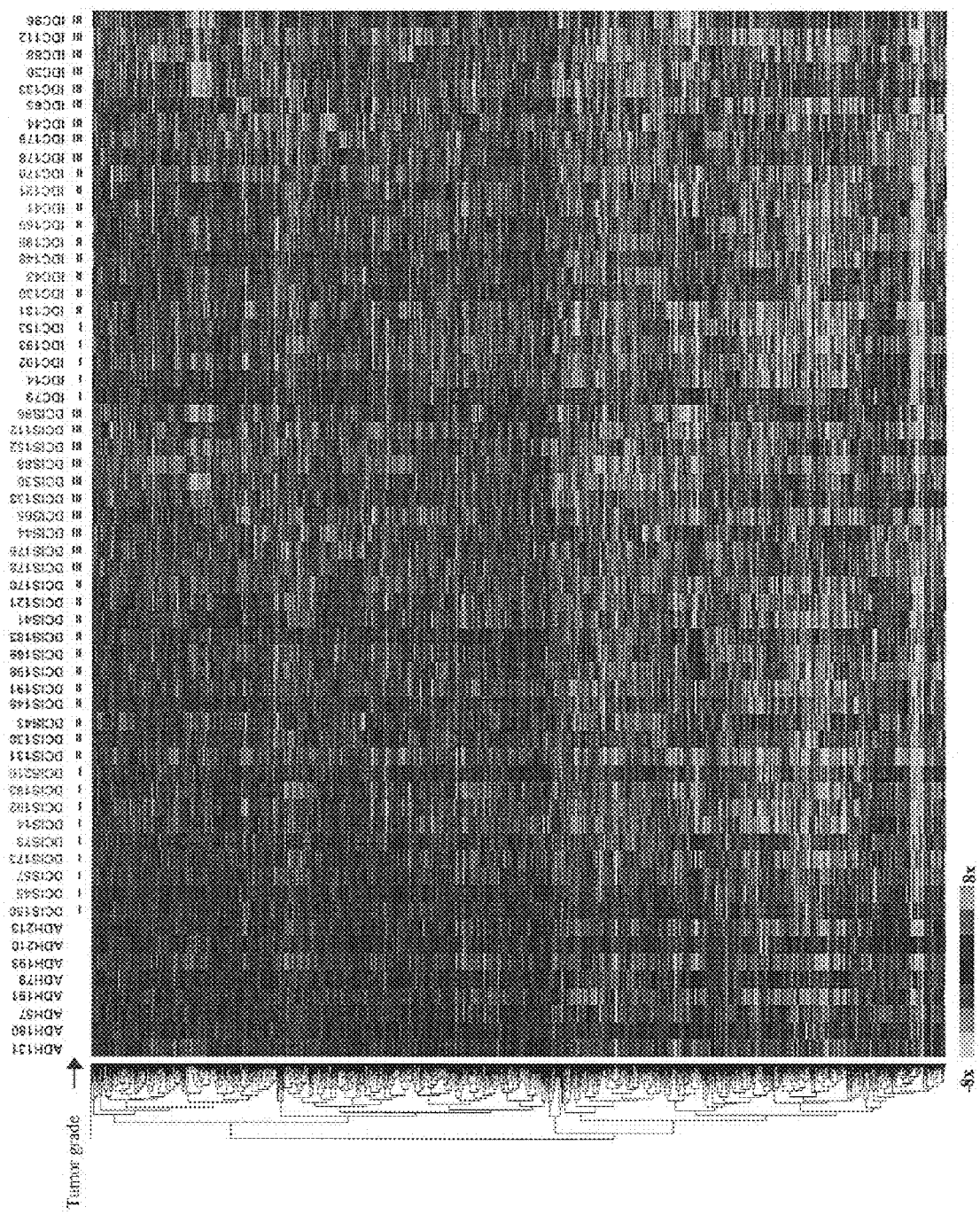

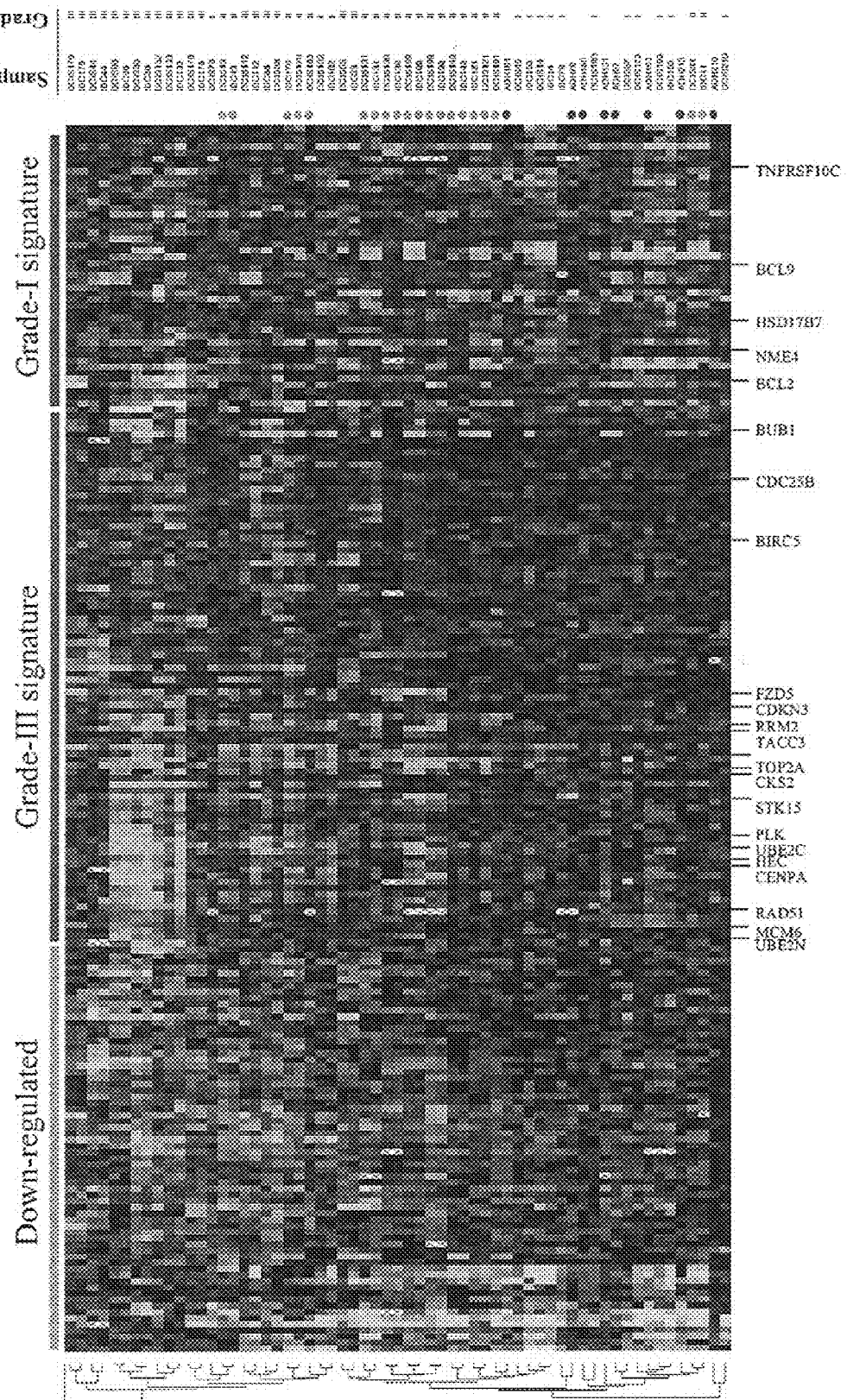

GRADING OF BREAST CANCER

RELATED APPLICATIONS

This application is a continuation-in-part of U.S. patent application Ser. No. 10/028,018 filed Dec. 21, 2001, which is hereby incorporated in its entirety as if fully set forth.

FIELD OF THE INVENTION

The invention relates to the identification and use of gene expression profiles, or patterns, involved in breast cancer progression. In particular, the invention provides the identities of genes that may be used to identify different grades of breast cancer within and between stages thereof. The gene expression profiles, whether embodied in nucleic acid expression, protein expression, or other expression formats, are used in the study and/or diagnosis of cells and tissue during breast cancer progression as well as for the study and/or determination of prognosis of a patient. When used for diagnosis or prognosis, the profiles are used to predict the status and/or phenotype of cells and tissues relative to breast cancer and the treatment thereof.

BACKGROUND OF THE INVENTION

Breast cancer is by far the most common cancer among women. Each year, more than 180,000 and 1 million women in the U.S. and worldwide, respectively, are diagnosed with breast cancer. Breast cancer is the leading cause of death for women between ages 50-55, and is the most common non-preventable malignancy in women in the Western Hemisphere. An estimated 2,167,000 women in the United States are currently living with the disease (National Cancer Institute, Surveillance Epidemiology and End Results (NCI SEER) program, *Cancer Statistics Review (CSR)*, www-seer-.ims.nci.nih.gov/Publications/CSR1973 (1998)). Based on cancer rates from 1995 through 1997, a report from the National Cancer Institute (NCI) estimates that about 1 in 8 women in the United States (approximately 12.8 percent) will develop breast cancer during her lifetime (NCI's Surveillance, Epidemiology, and End Results Program (SEER) publication *SEER Cancer Statistics Review* 1973-1997). Breast cancer is the second most common form of cancer, after skin cancer, among women in the United States. An estimated 250,100 new cases of breast cancer are expected to be diagnosed in the United States in 2001. Of these, 192,200 new cases of more advanced (invasive) breast cancer are expected to occur among women (an increase of 5% over last year), 46,400 new cases of early stage (in situ) breast cancer are expected to occur among women (up 9% from last year), and about 1,500 new cases of breast cancer are expected to be diagnosed in men (Cancer Facts & Figures 2001 American Cancer Society). An estimated 40,600 deaths (40,300 women, 400 men) from breast cancer are expected in 2001. Breast cancer ranks second only to lung cancer among causes of cancer deaths in women. Nearly 86% of women who are diagnosed with breast cancer are likely to still be alive five years later, though 24% of them will die of breast cancer after 10 years, and nearly half (47%) will die of breast cancer after 20 years.

Every woman is at risk for breast cancer. Over 70 percent of breast cancers occur in women who have no identifiable risk factors other than age (U.S. General Accounting Office. Breast Cancer, 1971-1991: Prevention, Treatment and Research. GAO/PEMD-92-12; 1991). Only 5 to 10% of breast cancers are linked to a family history of breast cancer (Henderson IC, Breast Cancer. In: Murphy G P, Lawrence W L, Lenhard RE (eds). *Clinical Oncology*. Atlanta, Ga.: American Cancer Society; 1995:198-219).

Each breast has 15 to 20 sections called lobes. Within each lobe are many smaller lobules. Lobules end in dozens of tiny bulbs that can produce milk. The lobes, lobules, and bulbs are all linked by thin tubes called ducts. These ducts lead to the nipple in the center of a dark area of skin called the areola. Fat surrounds the lobules and ducts. There are no muscles in the breast, but muscles lie under each breast and cover the ribs. Each breast also contains blood vessels and lymph vessels. The lymph vessels carry colorless fluid called lymph, and lead to the lymph nodes. Clusters of lymph nodes are found near the breast in the axilla (under the arm), above the collarbone, and in the chest.

Breast tumors can be either benign or malignant. Benign tumors are not cancerous, they do not spread to other parts of the body, and are not a threat to life. They can usually be removed, and in most cases, do not come back. Malignant tumors are cancerous, and can invade and damage nearby tissues and organs. Malignant tumor cells may metastasize, entering the bloodstream or lymphatic system. When breast cancer cells metastasize outside the breast, they are often found in the lymph nodes under the arm (axillary lymph nodes). If the cancer has reached these nodes, it means that cancer cells may have spread to other lymph nodes or other organs, such as bones, liver, or lungs.

Major and intensive research has been focussed on early detection, treatment and prevention. This has included an emphasis on determining the presence of precancerous or cancerous ductal epithelial cells. These cells are analyzed, for example, for cell morphology, for protein markers, for nucleic acid markers, for chromosomal abnormalities, for biochemical markers, and for other characteristic changes that would signal the presence of cancerous or precancerous cells. This has led to various molecular alterations that have been reported in breast cancer, few of which have been well characterized in human clinical breast specimens. Molecular alterations include presence/absence of estrogen and progesterone steroid receptors, HER-2 expression/amplification (Mark H F, et al. HER-2/neu gene amplification in stages I-IV breast cancer detected by fluorescent in situ hybridization. Genet Med; 1(3):98-103 1999), Ki-67 (an antigen that is present in all stages of the cell cycle except G0 and used as a marker for tumor cell proliferation, and prognostic markers (including oncogenes, tumor suppressor genes, and angiogenesis markers) like p53, p27, Cathepsin D, pS2, multi-drug resistance (MDR) gene, and CD31.

Examination of cells by a trained pathologist has also been used to establish whether ductal epithelial cells are normal (i.e. not precancerous or cancerous or having another non-cancerous abnormality), precancerous (i.e. comprising hyperplasia, atypical ductal hyperplasia (ADH)) or cancerous (comprising ductal carcinoma in situ, or DCIS, which includes low grade ductal carcinoma in situ, or LG-DCIS, and high grade ductal carcinoma in situ, or HG-DCIS) or invasive (ductal) carcinoma (IDC). Pathologists may also identify the occurrence of lobular carcinoma in situ (LCIS) or invasive lobular carcinoma (ILC). Breast cancer progression may be viewed as the occurrence of abnormal cells, such as those of ADH, DCIS, IDC, LCIS, and/or ILC, among normal cells.

It remains unclear whether normal cells become hyperplastic (such as ADH) and then progressing on to become malignant (DCIS, IDC, LCIS, and/or ILC) or whether normal cells are able to directly become malignant without transitioning through a hyperplastic stage. It has been observed, however, that the presence of ADH indicates a higher likelihood of developing a malignancy. This has resulting in treatment of patients with ADH to begin treatment with an antineoplastic/antitumor agent such as tamoxifen. This is in contrast to the treatment of patients with malignant breast cancer which usually includes surgical removal.

The rational development of preventive, diagnostic and therapeutic strategies for women at risk for breast cancer would be aided by a molecular map of the tumorigenesis process. Relatively little is known of the molecular events that mediate the transition of normal breast cells to the various stages of breast cancer progression. Similarly, little is known of the molecular events that mediate the transition of cells from one stage of breast cancer to another.

Molecular means of identifying the differences between normal, non-cancerous cells and cancerous cells (in general) have been the focus of intense study. The use of cDNA libraries to analyze differences in gene expression patterns in normal versus tumorigenic cells has been described (U.S. Pat. No. 4,981,783). DeRisi et al. (1996) describe the analysis of gene expression patterns between two cell lines: UACC-903, which is a tumorigenic human melanoma cell line, and UACC-903(+6), which is a chromosome 6 suppressed non-tumorigenic form of UACC-903. Labeled cDNA probes made from mRNA from these cell lines were applied to DNA microarrays containing 870 different cDNAs and controls. Genes that were preferentially expressed in one of the two cell lines were identified.

Golub et al. (1999) describe the use of gene expression monitoring as means to cancer class discovery and class prediction between acute myeloid leukemia (AML) and acute lymphoblastic leukemia (ALL). Their approach to class predictors used a neighborhood analysis followed by cross-validation of the validity of the predictors by withholding one sample and building a predictor based only on the remaining samples. This predictor is then used to predict the class of the withheld sample. They also used cluster analysis to identify new classes (or subtypes) within the AML and ALL.

Gene expression patterns in human breast cancers have been described by Perou et al. (1999), who studied gene expression between cultured human mammary epithelia cells (HMEC) and breast tissue samples by use of microarrays comprising about 5000 genes. They used a clustering algorithm to identify patterns of expression in HMEC and tissue samples. Perou et al. (2000) describe the use of clustered gene expression profiles to classify subtypes of human breast tumors. Hedenfalk et al. describe gene expression profiles in BRCA1 mutation positive, BRCA2 mutation positive, and sporadic tumors. Using gene expression patterns to distinguish breast tumor subclasses and predict clinical implications is described by Sorlie et al. and West et al.

All of the above described approaches, however, utilize heterogeneous populations of cells found in culture or in a biopsy to obtain information on gene expression patterns. The use of such populations may result in the inclusion or exclusion of multiple genes from the patterns. For this and the lack of statistical robustness reasons, the gene expression patterns observed by the above described approaches provide little confidence that the differences in gene expression may be meaningfully associated with the stages of breast cancer.

Citation of documents herein is not intended as an admission that any is pertinent prior art. All statements as to the date or representation as to the contents of documents is based on the information available to the applicant and does not constitute any admission as to the correctness of the dates or contents of the documents.

SUMMARY OF THE INVENTION

The present invention relates to the identification and use of gene expression patterns (or profiles or "signatures") which are correlated with (and thus able to discriminate between) cells in various stages and/or grades of breast cancer. Broadly defined, these stages are non-malignant versus malignant, but may also be viewed as normal versus atypical (optionally including reactive and pre-neoplastic) versus cancerous. Another definition of the stages is normal versus precancerous (e.g. atypical ductal hyperplasia (ADH) or atypical lobular hyperplasia (ALH)) versus cancerous (e.g. carcinoma in situ such as DCIS and/or LCIS) versus invasive (e.g. carcinomas such as IDC and/or ILC). The invention may also be applied to discriminations between normal and non-normal (including cancerous and other non-normal cells).

The invention also relates to the identification and use of gene expression patterns (or profiles or "signatures") which are correlated with (and thus able to discriminate between) cells in various grades (within one or more stage) of breast cancer. Grading of breast cancer is normally done for cases of invasive ductal carcinoma (IDC), and may be done for invasive lobular carcinoma (ILC) as well, where cytological criteria such as the Nottingham BSR, nuclear morphology, tissue architecture, proliferation index (such as assays for PCNA or Ki67), and extent of differentiation are used to assign a grade of I, II or III to particular breast cancer samples. Grade I is usually where the cells are still well differentiated and are usually positive for the estrogen receptor (ER). Grade III is usually where the cells are poorly differentiated and usually negative for ER. Grade II is generally where the cells have characteristics intermediate between grades I and III and can make up approximately 60% of all samples assayed. This is rather unfortunate because determination of grade in IDC is used directly for decisions on patient care.

Grading of cases of ductal carcinoma in situ (DCIS) is also possible, but is not routine in current clinical practice. Grading of lobular carcinoma in situ (LCIS) is also possible. In addition to grades I to III, conventional grading schemes may use the terms "low grade" and/or "high grade".

The present invention provides a non-subjective means for the identification of grades of various stages of cancer by assaying for the expression patterns associated with particular grades. Thus where subjective interpretation is used in grade assessment by pathologists using cytological criteria, the present invention provides objective gene expression patterns, which may optionally be performed in the absence of grading by histomorphological or cytological criteria, that are correlated with grades I-III (or low to high grade) to provide a more accurate assessment of breast cancer progression. The expression patterns of the invention thus provide a means to determine breast cancer prognosis. Furthermore, the expression patterns can also be used as a means to assay small, node negative tumors that are not readily graded by conventional means.

The gene expression patterns comprise one or more than one gene capable of discriminating between various stages and/or grades of breast cancer with significant accuracy. The gene(s) are identified as correlated with various stages and/or grades of breast cancer such that the levels of their expression are relevant to a determination of the stage and/or grade of breast cancer of a cell. Thus in one aspect, the invention provides a method to determine the stage and/or grade of breast cancer of a subject afflicted with, or suspected of having, breast cancer by assaying a cell containing sample from said subject for expression of one or more than one gene disclosed herein as correlated with one or more stages and/or grades of breast cancer.

Gene expression patterns of the invention are identified by analysis of gene expression in multiple samples of each stage and/or grade to be studied. The overall gene expression profile of a sample is obtained through quantifying the expression levels of mRNA corresponding to approximately 12000 genes. This overall profile is then analyzed to identify genes that are positively, or negatively, correlated, with a stage and/or grade of breast cancer. An expression profile of a subset of human genes may then be identified by the methods of the present invention as correlated with a particular stage and/or grade of breast cancer. The use of multiple samples increases the confidence which a gene may be believed to be correlated with a particular stage and/or grade. Without sufficient confidence, it remains unpredictable whether a particular gene is actually correlated with a stage and/or grade of breast cancer and also unpredictable whether a particular gene may be successfully used to identify the stage and/or grade of an unknown breast cancer cell sample.

A profile of genes that are highly correlated with one stage and/or grade relative to another may be used to assay an sample from a subject afflicted with, or suspected of having, breast cancer to identify the stage and/or grade of breast cancer to which the sample belongs. Such an assay may be used as part of a method to determine the therapeutic treatment for said subject based upon the stage(s) and/or grade(s) of breast cancer identified. The present invention thus also provides for the advantageous ability to determine grade of a stage of breast cancer in combination with stage information to provide more detailed information in diagnosing and treating breast cancer. This has not always been possible in the diagnosis and treatment of breast cancer using previous protocols, where it was often only possible to determine stage with grade being only occasionally determinable.

The correlated genes may be used singly with significant accuracy or in combination to increase the ability to accurately discriminate between various stages and/or grades of breast cancer. The present invention thus provides means for correlating a molecular expression phenotype with a physiological (cellular) stage or state. This correlation provides a way to molecularly diagnose and/or monitor a cell's status in comparison to different cancerous versus non-cancerous phenotypes as disclosed herein. Additional uses of the correlated gene(s) are in the classification of cells and tissues; determination of diagnosis and/or prognosis; and determination and/or alteration of therapy.

The ability to discriminate is conferred by the identification of expression of the individual genes as relevant and not by the form of the assay used to determine the actual level of expression. An assay may utilize any identifying feature of an identified individual gene as disclosed herein as long as the assay reflects, quantitatively or qualitatively, expression of the gene. Identifying features include, but are not limited to, unique nucleic acid sequences used to encode (DNA), or express (RNA), said gene or epitopes specific to, or activities of, a protein encoded by said gene. All that is required is the identity of the gene(s) necessary to discriminate between stages and/or grades of breast cancer and an appropriate cell containing sample for use in an expression assay.

In one aspect, the invention provides for the identification of the gene expression patterns by analyzing global, or near global, gene expression from single cells or homogenous cell populations which have been dissected away from, or otherwise isolated or purified from, contaminating cells beyond that possible by a simple biopsy. Because the expression of numerous genes fluctuate between cells from different patients as well as between cells from the same patient sample, multiple individual gene expression patterns are used as reference data to generate models which in turn permit the identification of individual gene(s) that are most highly correlated with particular breast cancer stages, and/or grades, and/or have the best the ability to discriminate cells of one stage and/or grade from another.

Use of the present invention has resulted in the identification of two major changes in gene expression, one of which is associated with the transition of normal breast cells to ADH (and persisting in a majority of DCIS and IDC cells), and the second is associated with tumor grade progression. The invention also provides the identification of a subset of genes that differ quantitatively in expression between DCIS and IDC cells.

In another aspect, the invention provides physical and methodological means for detecting the expression of gene(s) identified by the models generated by individual expression patterns. These means may be directed to assaying one or more aspect of the DNA template(s) underlying the expression of the gene(s), of the RNA used as an intermediate to express the gene(s), or of the proteinaceous product expressed by the gene(s).

In a further aspect, the gene(s) identified by a model as capable of discriminating between breast cancer stages and/or grades may be used to identify the cellular state of an unknown sample of cell(s) from the breast. Preferably, the sample is isolated via non-invasive means. The expression of said gene(s) in said unknown sample may be determined and compared to the expression of said gene(s) in reference data of gene expression patterns from the various stages and/or grades of breast cancer. Optionally, the comparison to reference samples may be by comparison to the model(s) constructed based on the reference samples.

One advantage provided by the present invention is that contaminating, non-breast cells (such as infiltrating lymphocytes or other immune system cells) are not present to possibly affect the genes identified or the subsequent analysis of gene expression to identify the status of suspected breast cancer cells. Such contamination is present where a biopsy is used to generate gene expression profiles.

While the present invention has been described mainly in the context of human breast cancer, it may be practiced in the context of breast cancer of any animal known to be potentially afflicted by breast cancer. Preferred animals for the application of the present invention are mammals, particularly those important to agricultural applications (such as, but not limited to, cattle, sheep, horses, and other "farm animals") and for human companionship (such as, but not limited to, dogs and cats).

BRIEF DESCRIPTION OF THE FIGURES

FIGS. 2a and 2b. Expression profiles of breast cancer progression. 2a. Data matrix of 1940 genes by breast cancer samples of different pathological stages. Columns represent samples of tissues identified as ADH; grades I, II, or III of DCIS; and grades I, II, or III of IDC. Rows represent genes. Color scale shown at left bottom. Genes are ordered by hierarchical clustering, and samples are ordered by pathological stage and tumor grade. 2b. Examples of interesting clusters I, II and III.

FIG. 3. Two-dimensional clustering of 62 samples and 200 genes correlated with tumor grade. Genes (columns) and samples (rows) were clustered independently using a hierarchical clustering algorithm. Red dots indicate ADH samples and green dots indicate grade II samples (DCIS or IDC). Three main clusters (down regulated, Grade III signature, and Grade I signature) are highlighted by color bars. See FIG. 2A for color scale.

FIG. 5. Breast cancer progression model. Breast cancer initiates within normal epithelium evolving into ADH, which progresses into grade I DCIS. A simultaneous 2-dimensional process drives tumor grade progression from I to II to III and stage progression from DCIS to IDC.

DETAILED DESCRIPTION OF THE SPECIFIC EMBODIMENTS

Definitions of Terms as Used Herein

Figure 1:
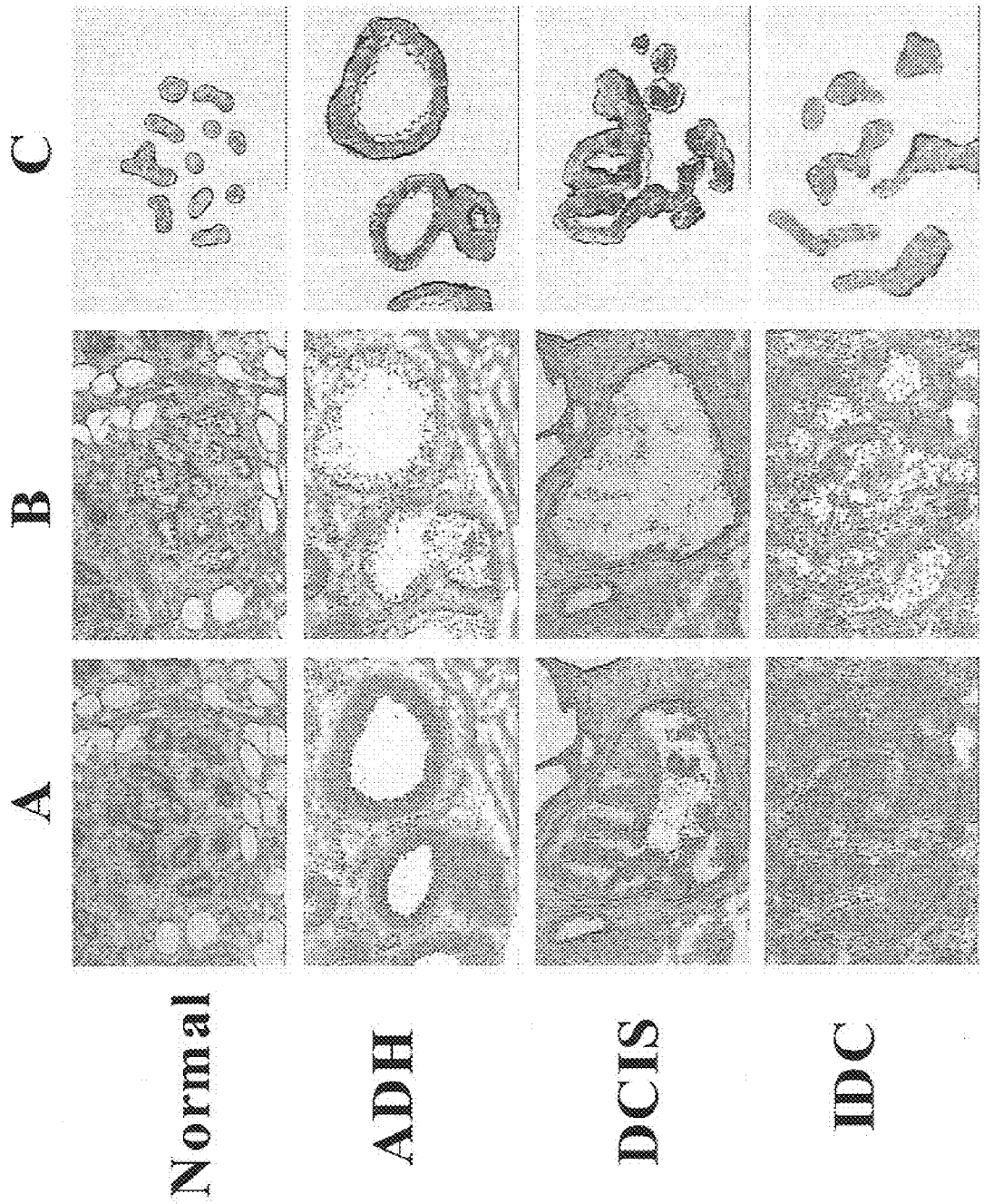
FIG. 1. Laser capture microdissection. Phenotypically normal breast epithelium and phenotypically abnormal epithelium from atypical ductal hyperplasia (ADH), ductal carcinoma in situ (DCIS) and invasive ductal carcinoma (IDC) from a single breast specimen (case 79) were captured from hematoxylin and eosin-stained sections (8 m in thickness). Panels A, B and C show the images of pre-capture, post-capture, and the captured epithelial compartments, respectively.

A gene expression "pattern" or "profile" or "signature" refers to the relative expression of a gene between two or more stages of breast cancer which is correlated with being able to distinguish between said stages.

A "gene" is a polynucleotide that encodes a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis.

A "stage" or "stages" (or equivalents thereof) of breast cancer refer to a physiologic state of a breast cell as defined by known cytological or histological (including immunohistology, histochemistry, and immunohistochemistry) procedures and are readily known to skilled in the art. Non-limiting examples include normal versus abnormal, non-cancerous versus cancerous, the different stages described herein (e.g. hyperplastic, carcinoma, and invasive), and grades within different stages (e.g. grades I, II, or III or the equivalents thereof within cancerous stages).

The terms "correlate" or "correlation" or equivalents thereof refer to an association between expression of one or more genes and a physiologic state of a breast cell to the exclusion of one or more other stages and/or identified by use of the methods as described herein. A gene may be expressed at higher or lower levels and still be correlated with one or more breast cancer stages.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

The term "amplify" is used in the broad sense to mean creating an amplification product can be made enzymatically with DNA or RNA polymerases. "Amplification," as used herein, generally refers to the process of producing multiple copies of a desired sequence, particularly those of a sample. "Multiple copies" mean at least 2 copies. A "copy" does not necessarily mean perfect sequence complementarity or identity to the template sequence.

By corresponding is meant that a nucleic acid molecule shares a substantial amount of sequence identity with another nucleic acid molecule. Substantial amount means at least 95%, usually at least 98% and more usually at least 99%, and sequence identity is determined using the BLAST algorithm, as described in Altschul et al. (1990), J. Mol. Biol. 215:403-410 (using the published default setting, i.e. parameters w=4, t=17). Methods for amplifying mRNA are generally known in the art, and include reverse transcription PCR (RT-PCR) and those described in U.S. patent application Ser. No. 10/942,252 entitled "Nucleic Acid Amplification" filed on Oct. 25, 2001 as well as U.S. Provisional Patent Applications 60/298,847 (filed Jun. 15, 2001) and 60/257,801 (filed Dec. 22, 2000), all of which are hereby incorporated by reference in their entireties as if fully set forth. Another method which may be used is quantitative PCR (or Q-PCR). Alternatively, RNA may be directly labeled as the corresponding cDNA by methods known in the art.

A "microarray" is a linear or two-dimensional array of preferably discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, preferably at least about $50/cm^2$, more preferably at least about $100/cm^2$, even more preferably at least about $500/cm^2$, but preferably below about $1,000/cm^2$. Preferably, the arrays contain less than about 500, about 1000, about 1500, about 2000, about 2500, or about 3000 immobilized polynucleotides in total. As used herein, a DNA microarray is an array of oligonucleotides or polynucleotides placed on a chip or other surfaces used to hybridize to amplified or cloned polynucleotides from a sample. Since the position of each particular group of primers in the array is known, the identities of a sample polynucleotides can be determined based on their binding to a particular position in the microarray.

Because the invention relies upon the identification of genes that are over- or under-expressed, one embodiment of the invention involves determining expression by hybridization of mRNA, or an amplified or cloned version thereof, of a sample cell to a polynucleotide that is unique to a particular gene sequence. Preferred polynucleotides of this type contain at least about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. Even more preferred are polynucleotides of at least or about 50, at least or about 100, at least about or 150, at least or about 200, at least or about 250, at least or about 300, at least or about 350, or at least or about 400 basepairs of a gene sequence that is not found in other gene sequences. The term "about" as used in the preceding sentence refers to an increase or decrease of 10% from the stated numerical value. Such polynucleotides may also be referred to as polynucleotide probes that are capable of hybridizing to sequences of the genes, or unique portions thereof, described herein. Preferably, the sequences are those of mRNA encoded by the genes, the corresponding cDNA to such mRNAs, and/or amplified versions of such sequences. In preferred embodiments of the invention, the polynucleotide probes are immobilized on an array, other devices, or in individual spots that localize the probes.

Alternatively, and in another embodiment of the invention, gene expression may be determined by analysis of expressed protein in a cell sample of interest by use of one or more antibodies specific for one or more epitopes of individual gene products (proteins) in said cell sample. Such antibodies are preferably labeled to permit their easy detection after binding to the gene product.

The term "label" refers to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

As used herein, a "breast tissue sample" or "breast cell sample" refers to a sample of breast tissue or fluid isolated from an individual suspected of being afflicted with, or at risk of developing, breast cancer. Such samples are primary isolates (in contrast to cultured cells) and may be collected by any non-invasive means, including, but not limited to, ductal lavage, fine needle aspiration, needle biopsy, the devices and methods described in U.S. Pat. No. 6,328,709, or any other suitable means recognized in the art. Alternatively, the "sample" may be collected by an invasive method, including, but not limited to, surgical biopsy.

"Expression" and "gene expression" include transcription and/or translation of nucleic acid material.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because the present invention is based on the relative level of gene expression, mutations in non-coding regions of genes as disclosed herein may also be assayed in the practice of the invention.

"Detection" includes any means of detecting, including direct and indirect detection of gene expression and changes therein. For example, "detectably less" products may be observed directly or indirectly, and the term indicates any reduction (including the absence of detectable signal). Similarly, "detectably more" product means any increase, whether observed directly or indirectly.

Unless defined otherwise all technical and scientific terms used herein have the same meaning as commonly understood to one of ordinary skill in the art to which this invention belongs.

Specific Embodiments

The present invention relates to the identification and use of gene expression patterns (or profiles or "signatures") which discriminate between (or are correlated with) cells in various stages and/or grades of breast cancer. Such patterns may be determined by the methods of the invention by use of a number of reference cell or tissue samples, such as those reviewed by a pathologist of ordinary skill in the pathology of breast cancer, which reflect various stages and/or grades of breast cancer. Because the overall gene expression profile differs from person to person, cancer to cancer, and cancer cell to cancer cell, correlations between certain cell states and genes expressed or underexpressed may be made as disclosed herein to identify genes that are capable of discriminating between different breast cancer states.

The present invention may be practiced with any number of genes believed, or likely to be, differentially expressed in breast cancer cells. Approximately 12,000 genes were used to identify hundreds of genes capable of discriminating between various stages and/or grades of breast cancer as shown in the following Examples. The identification may be made by using expression profiles of various homogenous normal and breast cancer cell populations, which were isolated by microdissection, such as, but not limited to, laser capture microdissection (LCM) of 100-1000 cells. Each gene of the expression profile may be assigned weights based on its ability to discriminate between two or more stages and/or grades of breast cancer. The magnitude of each assigned weight indicates the extent of difference in expression between the two groups and is an approximation of the ability of expression of the gene to discriminate between the two groups (and thus stages and/or grades). The magnitude of each assigned weight also approximates the extent of correlation between expression of individual gene(s) and particular breast cancer stages and/or grades.

It should be noted that merely high levels of expression in cells from a particular stage or grade does not necessarily mean that a gene will be identified as having a high absolute weight value.

Genes with top ranking weights (in absolute terms) may be used to generate models of gene expressions that would maximally discriminate between the two groups. Alternatively, genes with top ranking weights (in absolute terms) may be used in combination with genes with lower weights without significant loss of ability to discriminate between groups. Such models may be generated by any appropriate means recognized in the art, including, but not limited to, cluster analysis, supported vector machines, neural networks or other algorithm known in the art. The models are capable of predicting the classification of a unknown sample based upon the expression of the genes used for discrimination in the models. "Leave one out" cross-validation may be used to test the performance of various models and to help identify weights (genes) that are uninformative or detrimental to the predictive ability of the models. Cross-validation may also be used to identify genes that enhance the predictive ability of the models.

The gene(s) identified as correlated with particular breast cancer stages and/or grades by the above models provide the ability to focus gene expression analysis to only those genes that contribute to the ability to identify a cell as being in a particular stage and/or grade of breast cancer relative to another stage or grade. The expression of other genes in a breast cancer cell would be relatively unable to provide information concerning, and thus assist in the discrimination of, different stages of breast cancer. For example, the cysteine-rich protein I (intestinal), identified by I.M.A.G.E. Consortium CloneID 1323448 ("The I.M.A.G.E. Consortium: An Integrated Molecular Analysis of Genomes and their Expression," Lennon et al., 1996, Genomics 33:151-152; see also image.11nl.gov) has been found to be useful in discriminations between normal and ADH cells (with persistence through DCIS and IDC) Thus expression of this gene would be utilized in models to discriminate between the above listed stages but not for discerning between other stages. This type of analysis is readily incorporated into algorithms used to generate models with reference gene expression data.

As will be appreciated by those skilled in the art, the models are highly useful with even a small set of reference gene expression data and can become increasingly accurate with the inclusion of more reference data although the incremental increase in accuracy will likely diminish with each additional datum. The preparation of additional reference gene expression data using genes identified and disclosed herein for discriminating between different stages and/or grades of breast cancer is routine and may be readily performed by the skilled artisan to permit the generation of models as described above to predict the status of an unknown sample based upon the expression levels of those genes.

To determine the (increased or decreased) expression levels of genes in the practice of the present invention, any method known in the art may be utilized. In one preferred embodiment of the invention, expression based on detection of RNA which hybridizes to the genes identified and disclosed herein is used. This is readily performed by any RNA detection or amplification+detection method known or recognized as equivalent in the art such as, but not limited to, reverse transcription-PCR, the methods disclosed in U.S. patent application Ser. No. 10/942,252 entitled "Nucleic Acid Amplification" filed on Oct. 25, 2001 as well as U.S. Provisional Patent Applications 60/298,847 (filed Jun. 15, 2001) and 60/257,801 (filed Dec. 22, 2000), and methods to detect the presence, or absence, of RNA stabilizing or destabilizing sequences.

Alternatively, expression based on detection of DNA status may be used. Detection of the DNA of an identified gene as methylated or deleted may be used for genes that have decreased expression in correlation with a particular breast cancer stage and/or grade. This may be readily performed by PCR based methods known in the art, including, but not limited to, Q-PCR. Conversely, detection of the DNA of an identified gene as amplified may be used for genes that have increased expression in correlation with a particular breast cancer stage and/or grade. This may be readily performed by PCR based, fluorescent in situ hybridization (FISH) and chromosome in situ hybridization (CISH) methods known in the art.

Expression based on detection of a presence, increase, or decrease in protein levels or activity may also be used. Detection may be performed by any immunohistochemistry (IHC) based, blood based (especially for secreted proteins), antibody (including autoantibodies against the protein) based, ex foliate cell (from the cancer) based, mass spectroscopy based, and image (including used of labeled ligand) based method known in the art and recognized as appropriate for the detection of the protein. Antibody and image based methods are additionally useful for the localization of tumors after determination of cancer by use of cells obtained by a non-invasive procedure (such as ductal lavage or fine needle aspiration), where the source of the cancerous cells is not known. A labeled antibody or ligand may be used to localize the carcinoma(s) within a patient.

A preferred embodiment using a nucleic acid based assay to determine expression is by immobilization of one or more of the genes identified herein on a solid support, including, but not limited to, a solid substrate as an array or to beads or bead based technology as known in the art. Alternatively, solution based expression assays known in the art may also be used. The immobilized gene(s) may be in the form of polynucleotides that are unique or otherwise specific to the gene(s) such that the polynucleotide would be capable of hybridizing to a DNA or RNA corresponding to the gene(s). These polynucleotides may be the full length of the gene(s) or be short sequences of the genes (up to one nucleotide shorter than the full length sequence known in the art by deletion from the 5' or 3' end of the sequence) that are optionally minimally interrupted (such as by mismatches or inserted non-complementary basepairs) such that hybridization with a DNA or RNA corresponding to the gene(s) is not affected.

The immobilized gene(s) may be used to determine the state of nucleic acid samples prepared from sample breast cell(s) for which the pre-cancer or cancer status is not known or for confirmation of a status that is already assigned to the sample breast cell(s). Without limiting the invention, such a cell may be from a patient suspected of being afflicted with, or at risk of developing, breast cancer. The immobilized polynucleotide(s) need only be sufficient to specifically hybridize to the corresponding nucleic acid molecules derived from the sample. While even a single correlated gene sequence may to able to provide adequate accuracy in discriminating between two breast cancer cell stages and/or grades, two or more, three or more, four or more, five or more, six or more, seven or more, eight or more, nine or more, ten or more, or eleven or more of the genes identified herein may be used as a subset capable of discriminating may be used in combination to increase the accuracy of the method. The invention specifically contemplates the selection of more than one, two or more, three or more, four or more, five or more, six or more, seven or more, eight or more, nine or more, ten or more, or eleven or more of the genes disclosed in the tables and figures herein for use as a subset in the identification of whether an unknown or suspicious breast cancer sample is normal or is in one or more stages and/or grades of breast cancer. Optionally, the genes used will not include CloneID 809507, which is also known as GenBank accession number AA454563, described as an EST with high similarity to CD63 but of unknown function.

In embodiments where only one or a few genes are to be analyzed, the nucleic acid derived from the sample breast cancer cell(s) may be preferentially amplified by use of appropriate primers such that only the genes to be analyzed are amplified to reduce contaminating background signals from other genes expressed in the breast cell. Alternatively, and where multiple genes are to be analyzed or where very few cells (or one cell) is used, the nucleic acid from the sample may be globally amplified before hybridization to the immobilized polynucleotides. Of course RNA, or the cDNA counterpart thereof may be directly labeled and used, without amplification, by methods known in the art.

The above assay embodiments may be used in a number of different ways to identify or detect the breast cancer stage and/or grade, if any, of a breast cancer cell sample from a patient. In many cases, this would reflect a secondary screen for the patient, who may have already undergone mammography or physical exam as a primary screen. If positive, the subsequent needle biopsy, ductal lavage, fine needle aspiration, or other analogous methods may provide the sample for use in the above assay embodiments. The present invention is particularly useful in combination with non-invasive protocols, such as ductal lavage or fine needle aspiration, to prepare a breast cell sample. The current analysis of ductal lavage samples is by cytological examination by a trained pathologist who classifies the samples in terms that are at least partly subjective: unsatisfactory (too few cells), benign (including fibrocystic change), atypical (or mild atypia), suspicious (or marked atypia), or malignant.

The present invention provides a more objective set of criteria, in the form of gene expression profiles of a discrete set of genes, to discriminate (or delineate) between meaningful stages and/or grades (or classes) of breast cancer cells. In particularly preferred embodiments of the invention, the assays are used to discriminate between the three grades (I, II, III) of carcinomas in situ as well as invasive carcinomas. With the use of alternative algorithms, such as neural networks, comparisons that discriminate between multiple (more than pairwise) classes may also be performed.

In one embodiment of the invention, the isolation and analysis of a breast cancer cell sample may be performed as follows:

(1) Ductal lavage or other non-invasive procedure is performed on a patient to obtain a sample.
(2) Sample is prepared and coated onto a microscope slide. Note that ductal lavage results in clusters of cells that are cytologically examined as stated above.
(3) Pathologist or image analysis software scans the sample for the presence of non-normal and/or atypical cells.
(4) If non-normal and/or atypical cells are observed, those cells are harvested (e.g. by microdissection such as LCM).
(5) RNA is extracted from the harvested cells.
(6) RNA is purified, amplified, and labeled.
(7) Labeled nucleic acid is contacted with a microarray containing polynucleotides of the genes identified herein as correlated to discriminations between two or more stages of breast cancer under hybridization conditions, then processed and scanned to obtain a pattern of intensities of each spot (relative to a control for general gene expression in cells) which determine the level of expression of the gene(s) in the cells.
(8) The pattern of intensities is analyzed by comparison to the expression patterns of the genes in known samples of normal and breast cancer cells (relative to the same control).

A specific example of the above method would be performing ductal lavage following a primary screen, observing and collecting non-normal and/or atypical cells for analysis. The comparison to known expression patterns, such as that made possible by a model generated by an algorithm (such as, but not limited to nearest neighbor type analysis, SVM, or neural networks) with reference gene expression data for the different breast cancer stages and/or grades, identifies the cells as being most likely grade III IDC.

Alternatively, the sample may permit the collection of both normal as well as non-normal and/or atypical cells for analysis. The gene expression patterns for each of these two samples will be compared to each other as well as the model and the normal versus individual abnormal comparisons therein based upon the reference data set. This approach can be significantly more powerful that the non-normal and/or atypical cells only approach because it utilizes significantly more information from the normal cells and the differences between normal and non-normal/atypical cells (in both the sample and reference data sets) to determine the status of the non-normal and/or atypical cells from the sample.

By appropriate selection of the genes used in the analysis, identification of the relative amounts of non-normal and/or atypical cells may also be possible, although in most clinical settings, the identification of the highest grade of breast cancer with confidence makes identification of lower grades less important. Stated differently, the identification of invasive cancer determines the clinical situation regardless of the presence of carcinoma in situ or hyperplastic cells, or the identification of carcinoma in situ makes determines the clinical situation regardless of the presence of hyperplastic cells. Similarly, the identification of a higher grade of cancer cells determines the clinical situation regardless of the presence of lower grades of cancer cells.

With use of the present invention, skilled physicians may prescribe treatments based on non-invasive samples that they would have prescribed for a patient which had previously received a diagnosis via a solid tissue biopsy.

The above discussion is also applicable where a palpable lesion is detected followed by fine needle aspiration or needle biopsy of cells from the breast. The cells are plated and reviewed by a pathologist or automated imaging system which selects cells for analysis as described above. This again provides a means of linking visual to molecular cytology and provides a less subjective means of identifying the physiological state of breast cancer cells without the need for invasive solid tissue biopsies.

The present invention may also be used, however, with solid tissue biopsies. For example, a solid biopsy may be collected and prepared for visualization followed by determination of expression of one or more genes identified herein to determine the stage of breast cancer, if any. One preferred means is by use of in situ hybridization with polynucleotide or protein identifying probe(s) for assaying expression of said gene(s).

In an alternative method, the solid tissue biopsy may be used to extract molecules followed by analysis for expression of one or more gene(s). This provides the possibility of leaving out the need for visualization and collection of only those cells suspected of being non-normal and/or atypical. This method may of course be modified such that only cells suspected of being non-normal and/or atypical are collected and used to extract molecules for analysis. This would require visualization and selection as an prerequisite to gene expression analysis.

In a further modification of the above, both normal cells and cells suspected of being non-normal and/or atypical are collected and used to extract molecules for analysis of gene expression. The approach, benefits and results are as described above using non-invasive sampling.

In a further alternative to all of the above, the gene(s) identified herein may be used as part of a simple PCR or array based assay simply to determine the presence of non-normal and/or atypical cells in a sample from a non-invasive sampling procedure. This is simple to perform and utilizes genes identified to be the best discriminators of normal versus abnormal cells without the need for any cytological examination. If no non-normal and/or atypical cells are identified, no cytological examination is necessary. If non-normal and/or atypical cells are identified, cytological examination follows, and a more comprehensive analysis, as described above, may follow.

The genes identified herein may be used to generate a model capable of predicting the breast cancer stage and/or grade (if any) of an unknown breast cell sample based on the expression of the identified genes in the sample. Such a model may be generated by any of the algorithms described herein or otherwise known in the art as well as those recognized as equivalent in the art using gene(s) (and subsets thereof) disclosed herein for the identification of whether an unknown or suspicious breast cancer sample is normal or is in one or more stages and/or grades of breast cancer. The model provides a means for comparing expression profiles of gene(s) of the subset from the sample against the profiles of reference data used to build the model. The model can compare the sample profile against each of the reference profiles or against model defining delineations made based upon the reference profiles. Additionally, relative values from the sample profile may be used in comparison with the model or reference profiles.

In a preferred embodiment of the invention, breast cell samples identified as normal and non-normal and/or atypical from the same subject may be analyzed for their expression profiles of the genes used to generate the model. This provides an advantageous means of identifying the stage of the abnormal sample based on relative differences from the expression profile of the normal sample. These differences can then be used in comparison to differences between normal and individual abnormal reference data which was also used to generate the model.

The detection of gene expression from the samples may be by use of a single microarray able to assay gene expression from all pairwise comparisons disclosed herein for convenience and accuracy.

Other uses of the present invention include providing the ability to identify breast cancer cell samples as being those of a particular stage and/or grade of cancer for further research or study. This provides a particular advantage in many contexts requiring the identification of breast cancer stage and/or grade based on objective genetic or molecular criteria rather than cytological observation. It is of particular utility to distinguish different grades of a particular breast cancer stage for further study, research or characterization because no objective criteria for such delineation was previously available.

The materials for use in the methods of the present invention are ideally suited for preparation of kits produced in accordance with well known procedures. The invention thus provides kits comprising agents for the detection of expression of the disclosed genes for identifying breast cancer stage. Such kits optionally comprising the agent with an identifying description or label or instructions relating to their use in the methods of the present invention, is provided. Such a kit may comprise containers, each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes of the present invention (e.g., appropriate length poly(T) or random primers linked to a promoter reactive with the RNA polymerase). A set of instructions will also typically be included.

The methods provided by the present invention may also be automated in whole or in part. All aspects of the present invention may also be practiced such that they consist essentially of a subset of the disclosed genes to the exclusion of material irrelevant to the identification of breast cancer stages in a cell containing sample.

Gene Expression Profiles of Pathological Stare and Histological Grade Progression of Human Breast Cancer To identify gene expression changes that occur during breast cancer progression, isolation via LCM phenotypically of abnormal epithelium from ADH, DCIS and IDC and phenotypically normal epithelium (henceforth referred to as normal) from 36 breast cancer patients and 3 healthy mammoplasty reduction patients (FIG. 1A and Table 1) was performed. The resulting 300 independently microdissected samples were used to interrogate a microarray containing approximately 12,000 human genes. Genes showing significant differences in the pair-wise comparisons of normal vs. ADH, normal vs. DCIS and normal vs. IDC were selected by linear discriminant analysis, resulting in a total of 1940 unique genes for further exploration.

TABLE 1

Patient and tumor characteristics of clinical samples in this study

| Case ID | Stages Microdissected | Age | ER | PR | HER2 | Node[a] |
|---|---|---|---|---|---|---|
| 8 | DCIS (III), IDC (III) | 48 | Pos | Pos | Pos | Pos |
| 14 | N, DCIS (I), IDC (I) | 44 | Pos | Pos | ND | Pos |
| 22 | ADH, DCIS (I) | 44 | ND | ND | ND | Pos |
| 25 | DCIS (I), IDC (II) | 81 | Pos | Neg | ND | ND |
| 30 | N, DCIS (III), IDC (III) | 47 | Neg | Neg | Neg | Pos |
| 41 | N, DCIS (II), IDC (II) | 55 | Pos | Pos | ND | Neg |
| 43 | N, DCIS (II), IDC (II) | 53 | Pos | Neg | Neg | Pos |
| 44 | N, DCIS (III), IDC (III) | 28 | Pos | Pos | Neg | Neg |
| 45 | N, DCIS (I) | 36 | Pos | Neg | Neg | Neg |
| [b]57 | N, ADH, DCIS (I) | 34 | ND | ND | ND | Neg |
| 65 | N, DCIS (III), IDC (III) | 39 | Pos | Pos | Neg | Neg |
| 78 | MPR | 46 | | | | |
| 79 | N, ADH, DCIS (I), IDC (I) | 54 | Pos | Pos | Neg | Pos |
| 88 | N, DCIS (III), IDC (III) | 35 | Pos | Pos | ND | Pos |
| 95 | MPR | 16 | | | | |
| 96 | N, DCIS (III), IDC (III) | 31 | Neg | Neg | Neg | Pos |
| 97 | DCIS (III), IDC (III) | 79 | Neg | Neg | Pos | Pos |
| 102 | N, DCIS (I), IDC (I) | 55 | Pos | Neg | Neg | Pos |
| 112 | N, DCIS (III), IDC (III) | 31 | Neg | Pos | Neg | Pos |
| 121 | N, DCIS (II), IDC (II) | 45 | Pos | Pos | Pos | Pos |
| 130 | N, DCIS (II), IDC (II) | 54 | Pos | Pos | Neg | Pos |
| 131 | N, ADH, DCIS (II), IDC (II) | 37 | Pos | Pos | Pos | Pos |
| 133 | N, DCIS (III), IDC (III) | 44 | Neg | Neg | Pos | Pos |
| 148 | N, DCIS (II), IDC (II) | 42 | Pos | Pos | Neg | Pos |
| [b]152 | N, DCIS (III) | 55 | ND | ND | ND | Neg |
| 153 | N, IDC (I) | 46 | Pos | Pos | Pos | Pos |
| 169 | N, DCIS (II), IDC (II) | 34 | Pos | Pos | Neg | Pos |
| 170 | N, DCIS (II), IDC (II) | 44 | Pos | Pos | Pos-FISH | Pos |
| 173 | N, DCIS (I), IDC (I) | 52 | Pos | Pos | Neg | Neg |
| 178 | N, DCIS (III), IDC (III) | 43 | Pos | Pos | Pos | Pos |
| 179 | N, DCIS (III), IDC (III) | 37 | Neg | Neg | Pos-FISH | Pos |
| 180 | N, ADH, DCIS (I), IDC (I) | 46 | Pos | Pos | Neg | Pos |
| 183 | N, DCIS (II) | 46 | ND | ND | ND | Pos |
| [b]191 | N, ADH, DCIS (II) | 43 | ND | ND | ND | |
| 193 | N, ADH, DCIS (I), IDC (I) | 45 | Pos | Pos | Neg | Pos |
| 198 | N, DCIS (II), IDC (II) | 30 | Pos | Pos | Neg | Neg |
| [b]210 | N, ADH, DCIS (I) | 62 | ND | ND | ND | Neg |
| [b]213 | N, ADH | 45 | ND | ND | ND | Neg |
| 215 | MPR | 30 | | | | |

[a]Nodal status. Tumor grades indicated by roman numerals in parenthesis after the pathological stage of the specimen.
Abbreviations used for pathological stages:
N, normal;
ADH, atypical ductal hyperplasia;
DCIS, ductal carcinoma in situ;
IDC, invasive ductal carcinoma;
MPR, mammoplasty reduction.
Abbreviations used for tumor marker status:
ND, not determined;
Pos, positive;
Neg, negative;
Pos-Fish, HER2-positivity by fluorescent in situ hybridization (FISH).
[b]Individuals with pre-invasive breast cancer only.

One important advantage of LCM is the ability to procure both normal and diseased cell populations from the same biopsy. Therefore, the expression level of each gene in a disease state (ADH or DCIS or IDC) is represented as the ratio to the patient-matched normal, which highlights differences due to disease state as opposed to the genetic background of a particular patient. Unsupervised hierarchical clustering of the 1940 genes based on the resulting data across all samples reveals two main clusters (See FIG. 2a). One cluster demonstrates increased expression in a majority of the diseased samples, and another cluster shows a relatively uniform decrease in expression across all samples. Importantly, most of these alterations (both increases and decreases) occur in the earliest stage of progression (ADH) and persist throughout later stages of DCIS and IDC. In addition, closer examination of this global view suggests that some of these genes increase their expression in DCIS/IDC of higher tumor grade. See Example II below.

Figure 2B:
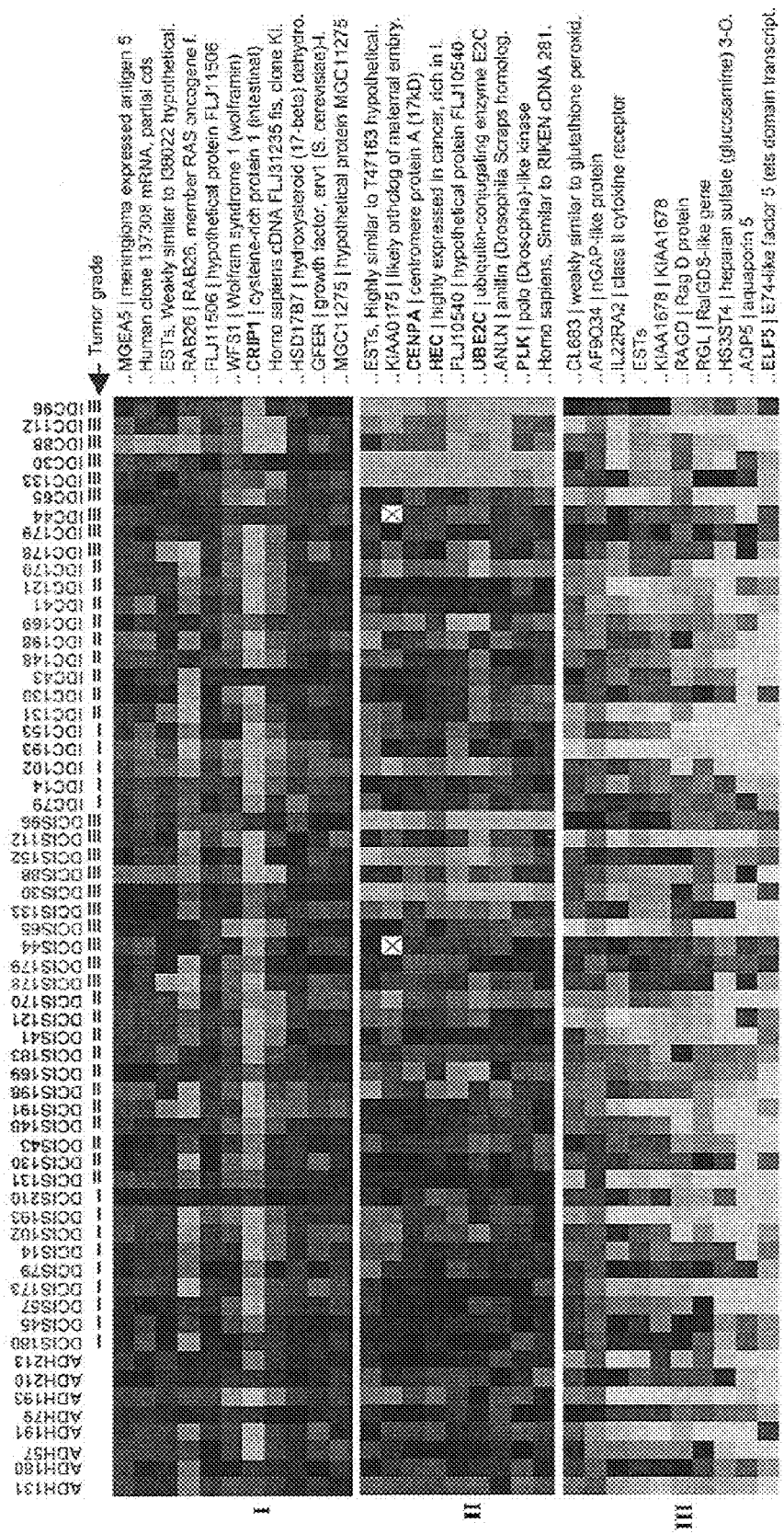

Three example clusters of genes further illustrate these points (FIG. 2b). Cluster I consists of genes whose expression levels increase in ADH and persist in a majority of DCIS and IDC samples. The gene CRIP1 is especially prominent and thus may be a potential biomarker for the detection of breast cancer including the pre-malignant stage of ADH. The genes of Cluster I along with their I.M.A.G.E. Consortium CloneID number and descriptive identifiers are listed in Table 2.

TABLE 2

| IMAGE CloneID | Description |
|---|---|
| 729975 | MGEA5 | meningioma expressed antigen 5 (hyaluronidase) |
| 241043 | Human clone 137308 mRNA, partial cds |
| 1556859 | ESTs, Weakly similar to I38022 hypothetical protein [*H. sapiens*] |
| 1911343 | RAB26 | RAB26, member RAS oncogene family |
| 589232 | FLJ11506 | hypothetical protein FLJ11506 |
| 138189 | WFS1 | Wolfram syndrome 1 (wolframin) |
| 1323448 | CRIP1 | cysteine-rich protein 1 (intestinal) |
| 488202 | *Homo sapiens* cDNA FLJ31235 fis, clone KIDNE2004681, moderately similar to *Mus musculus* peroxisomal long chain acyl-CoA thioesterase Ib (Pte1b) gene |
| 256619 | HSD17B7 | hydroxysteroid (17-beta) dehydrogenase 7 |
| 810063 | GFER | growth factor, erv1 (*S. cerevisiae*)-like (augmenter of liver regeneration) |
| 824879 | MGC11275 | hypothetical protein MGC11275 |

Genes in cluster II display an expression pattern that correlate with tumor grade with the highest expression in grade III DCIS/IDC. Cluster II includes several genes important in the cell cycle (CENPA, HEC, UBE2C and PLK), and their elevated expression in grade III DCIS/IDC may reflect the higher proliferative index of high-grade tumors. The genes of Cluster II along with their I.M.A.G.E. Consortium CloneID number and descriptive identifiers are listed in Table 3.

TABLE 3

| IMAGE CloneID | Description |
|---|---|
| 66406 | ESTs, Highly similar to T47163 hypothetical protein DKFZp762E1312.1 [*H. sapiens*] |
| 1517595 | KIAA0175 | likely ortholog of maternal embryonic leucine zipper kinase |
| 2017415 | CENPA | centromere protein A (17 kD) |
| 345787 | HEC | highly expressed in cancer, rich in leucine heptad repeats |
| 504308 | FLJ10540 | hypothetical protein FLJ10540 |
| 769921 | UBE2C | ubiquitin-conjugating enzyme E2C |

TABLE 3-continued

| IMAGE CloneID | Description |
|---|---|
| 128711 | ANLN | anillin (*Drosophila* Scraps homolog), actin binding protein |
| 744047 | PLK | polo (*Drosophila*)-like kinase |
| 128695 | *Homo sapiens*, Similar to RIKEN cDNA 1810054O13 gene, clone IMAGE: 3845933, mRNA, partial cds |

Genes in cluster III demonstrate decreased expression in all three pathological stages. The epithelium-specific transcription factor ELF5 is noteworthy since it maps to chromosome 11p13-15, a region subject to frequent loss of heterozygosity and rearrangement in multiple carcinoma including breast cancer (Zhou, J. et al. (1998a)). Therefore, loss of expression of ELF5 in ADH may be an important first step in the initiation of breast malignancy. Taken together, these results demonstrate that the normal to ADH transition is associated with extensive gene expression alterations and support the notion that ADH is a direct precursor to DCIS and IDC. The genes of Cluster III along with their I.M.A.G.E. Consortium CloneID number and descriptive identifiers are listed in Table 4.

TABLE 4

| IMAGE CloneID | Description |
|---|---|
| 768007 | CL683 | weakly similar to glutathione peroxidase 2 |
| 877621 | | nGAP-like protein |
| 1570670 | IL22RA2 | class II cytokine receptor |
| 1881774 | KIAA1678 | KIAA1678 |
| 1686766 | | Rag D protein |
| 505864 | RGL | RalGDS-like gene |
| 1569187 | HS3ST4 | heparan sulfate (glucosamine) 3-O-sulfotransferase 4 |
| 755881 | AQP5 | aquaporin 5 |
| 1864302 | ELF5 | E74-like factor 5 (ets domain transcription factor) |

To gain further insight into the observation that different histological grades may be associated with distinct gene expression signatures (FIG. 2b, cluster II), two sets of genes were identified. Each comprised 100 genes correlating with grade I and grade III samples respectively using discriminant analysis. Again, to cancel out potential differences in the absolute levels of expression among individuals, gene expression values were expressed as ratios of ADH, DCIS or IDC to the corresponding normal. Unsupervised two-dimensional clustering revealed three major gene clusters (FIG. 3). One cluster of genes demonstrated decreased expression in all samples with subtle quantitative differences between grade I and grade III (green bar). A second cluster of genes (denoted as the grade III signature) shows markedly increased expression in grade III samples (red bar), whereas a third cluster (grade I signature) demonstrates increased expression primarily in grade I samples (blue bar). The genes of "green bar" genes along with their I.M.A.G.E. Consortium CloneID number, chromosomal location and descriptive identifiers (if known) are listed in Table 5.

TABLE 5

| IMAGE Clone ID | Chromosomal location | Description |
|---|---|---|
| 471196 | 2q37 | ITM3 | integral membrane protein 3 |
| 796904 | 6q24-q25 | PLAGL1 | pleiomorphic adenoma gene-like 1 |
| 32493 | 2q31.1 | ITGA6 | "integrin, alpha 6" |
| 1534700 | 11q21 | KIAA0830 | KIAA0830 protein |
| 712139 | 2q37.2 | ARL7 | ADP-ribosylation factor-like 7 |
| 291478 | 1p36 | RUNX3 | runt-related transcription factor 3 |
| 150897 | 19p13.1 | B3GNT3 | "UDP-GlcNAc:betaGal beta-1,3-N-acetylglucosaminyltransferase 3" |
| 1653105 | 3p14-p12 | TSP50 | testes-specific protease 50 |
| 665384 | 16 | KIAA1609 | KIAA1609 protein |
| 842818 | 16q23-q24 | KARS | lysyl-tRNA synthetase |
| 37671 | 18q11.2 | FLJ21610 | hypothetical protein FLJ21610 |
| 773301 | 16q22.1 | CDH3 | "cadherin 3, type 1, P-cadherin (placental)" |
| 503671 | 6 | *Homo sapiens* cDNA FLJ14368 fis, clone HEMBA1001122 |
| 3172883 | 11 | ESTs, Weakly similar to S24195 dopamine receptor D4 [*H. sapiens*] |
| 684890 | 16p12.1 | FLJ20274 | hypothetical protein FLJ20274 |
| 593840 | 17q11.2 | DKFZP564K1964 | DKFZP564K1964 protein |
| 121454 | 17p13.1 | ALOX12 | arachidonate 12-lipoxygenase |
| 197913 | 1p34.2 | SFPQ | splicing factor proline/glutamine rich (polypyrimidine tract-binding protein-associated) |
| 43090 | 20q13.12 | H-L(3)MBT | lethal (3) malignant brain tumor l(3)mbt protein (*Drosophila*) homolog |
| 814826 | 2 | ESTs |
| 1635062 | 12q13.13 | DKFZP586A011 | DKFZP586A011 protein |
| 814815 | | |
| 1601845 | 7q22-q31.1 | CAPRI | Ca2+-promoted Ras inactivator |
| 190059 | 19p13.3 | GNG7 | "guanine nucleotide binding protein (G protein), gamma 7" |
| 277044 | 19q13.32 | KIAA1183 | KIAA1183 protein |
| 1592530 | 3p21.31 | IP6K2 | mammalian inositol hexakisphosphate kinase 2 |
| 431231 | 11q13 | EFEMP2 | EGF-containing fibulin-like extracellular matrix protein 2 |
| 267254 | 17 | ESTs, Highly similar to LOX2_HUMAN ARACHIDONATE 12-LIPOXYGENASE [*H. sapiens*] |
| 43679 | 10 | ESTs |
| 295572 | 12q24.21 | KIAA0682 | KIAA0682 gene product |
| 46129 | 12q13.1 | HDAC7A | histone deacetylase 7A |
| 1569077 | 6 | EST |
| 138242 | 1 | ESTs, Moderately similar to MAS2_human mannan-binding lectin serine protease 2 precursor [*H. sapiens*] |
| 417637 | 4p16 | KIAA1276 | KIAA1276 protein |
| 248631 | 3p21.2-p21.1 | AMT | aminomethyltransferase (glycine cleavage system protein T) |
| 1553530 | 2 | KIAA0788 | KIAA0788 protein |
| 307029 | | |
| 1883169 | 5p15.32 | FLJ20303 | hypothetical protein FLJ20303 |
| 345764 | 3p23 | SATB1 | special AT-rich sequence binding protein 1 (binds to nuclear matrix/scaffold-associating DNA's) |
| 703964 | 11q23 | INPPL1 | inositol polyphosphate phosphatase-like 1 |
| 70349 | Xq13.1 | MLLT7 | "myeloid/lymphoid or mixed-lineage leukemia (trithorax (*Drosophila*) homolog); translocated to, 7" |
| 1868349 | 15q11.2-q21.3 | PLA2G4B | "phospholipase A2, group IVB (cytosolic)" |
| 126466 | 1p34.1 | KIAA0467 | KIAA0467 protein |
| 1631682 | 1p32 | PPIE | peptidylprolyl isomerase E (cyclophilin E) |
| 172783 | 19 | ZNF358 zinc finger protein 358 |
| 1566877 | 11q13 | C11orf2 | chromosome 11 open reading frame2 |
| 1630990 | 3p21.3-p21.2 | RPL29 | ribosomal protein L29 |
| 283124 | 19 | *Homo sapiens*, clone IMAGE: 3917549, mRNA, partial cds |
| 126415 | 10 | *Homo sapiens* mRNA; cDNA DKFZp566H0124 (from clone DKFZp566H0124) |
| 344168 | 10q23 | POLL | "polymerase (DNA directed), lambda" |
| 823634 | 10 | ESTs |
| 325583 | | EST |
| 810741 | 17p13.2 | GABARAP | GABA(A) receptor-associated protein |
| 511831 | 3 | MGC12936 | hypothetical protein MGC12936 |
| 180561 | 1p13.3 | GSTM1 | glutathione S-transferase M1 |
| 206217 | 11p11.2 | NR1H3 | "nuclear receptor subfamily 1, group H, member 3" |
| 108667 | 22q12.2 | SF3A1 | "splicing factor 3a, subunit 1, 120 kD" |
| 839796 | 12p13.31 | LOC51147 | candidate tumor suppressor p33 ING1 homolog |
| 502518 | 3p21 | LAMB2 | "laminin, beta 2 (laminin S)" |
| 810981 | 22q13 | FLJ20699 | hypothetical protein FLJ20699 |
| 1635059 | 9 | *Homo sapiens*, clone MGC: 16638 IMAGE: 4121964, mRNA, complete cds |
| 767176 | 17p13.1 | TNFSF13 | "tumor necrosis factor (ligand) superfamily, member 13" |
| 810358 | 17p13-p11 | ACADVL | "acyl-Coenzyme A dehydrogenase, very long chain" |
| 2757710 | 10p11.2 | ZNF37A | zinc finger protein 37a (KOX 21) |
| 1652259 | 7q31.3 | LKR/SDH | lysine-ketoglutarate reductase/saccharopine dehydrogenase |

The genes of "red bar" genes along with their I.M.A.G.E. Consortium CloneID number, chromosomal location and descriptive identifiers (if known) are listed in Table 6.

TABLE 6

| IMAGE Clone ID | Chromosomal location | Description |
|---|---|---|
| 293727 | 22q13.2 | MGC861 | hypothetical protein MGC861 |
| 843121 | 6p22.1-p21.2 | CLIC1 | chloride intracellular channel 1 |
| 839682 | 12q22 | UBE2N | ubiquitin-conjugating enzyme E2N (homologous to yeast UBC13) |
| 815501 | 19p13.3 | MGC2721 | hypothetical protein MGC2721 |
| 1587847 | 2q21 | MCM6 | "minichromosome maintenance deficient (mis5, *S. pombe*) 6" |
| 1416055 | 8 | KIAA0165 | "extra spindle poles, *S. cerevisiae*, homolog of" |
| 2018131 | 12p13.2-p13.1 | RACGAP1 | Rac GTPase activating protein 1 |
| 1476053 | 15q15.1 | RAD51 | RAD51 (*S. cerevisiae*) homolog (*E coli* RecA homolog) |
| 869375 | 15q26.1 | IDH2 | "isocitrate dehydrogenase 2 (NADP+), mitochondrial" |
| 951241 | 15q13.3 | ANKT | nucleolar protein ANKT |
| 743810 | 12p13 | MGC2577 | hypothetical protein MGC2577 |
| 292936 | 1p34.3 | FLJ10468 | hypothetical protein FLJ10468 |
| 66406 | 2 | ESTs, Highly similar to T47163 hypothetical protein DKFZp762E1312.1 [*H. sapiens*] |
| 1517595 | 9p11.2 | KIAA0175 | likely ortholog of maternal embryonic leucine zipper kinase |
| 2017415 | 2p24-p21 | CENPA | centromere protein A (17 kD) |
| 345787 | 18p11.31 | HEC | "highly expressed in cancer, rich in leucine heptad repeats" |
| 504308 | 10cen-q26.11 | FLJ10540 | hypothetical protein FLJ10540 |
| 769921 | 20q13.12 | UBE2C | ubiquitin-conjugating enzyme E2C |
| 128711 | 7p15-p14 | ANLN | "anillin (*Drosophila* Scraps homolog), actin binding protein" |
| 744047 | 16p12.3 | PLK | polo (*Drosophila*)-like kinase |
| 564981 | 18 | *Homo sapiens*, Similar to RIKEN cDNA 2810433K01 gene, clone MGC: 10200 IMAGE: 3909951, mRNA, complete cds |
| 259950 | 8q23 | CML66 | chronic myelogenous leukemia tumor antigen 66 |
| 825606 | 10q24.1 | KNSL1 | kinesin-like 1 |
| 814270 | 4q27 | PMSCL1 | polymyositis/scleroderma autoantigen 1 (75 kD) |
| 785368 | 8p21-p12 | TOPK | PDZ-binding kinase; T-cell originated protein kinase |
| 209066 | 20q13.2-q13.3 | STK15 | serine/threonine kinase 15 |
| 739450 | 1q21.2 | LASS2 | "longevity assurance (LAG1, *S. cerevisiae*) homolog 2" |
| 1702742 | 16q24.3 | SLC7A5 | "solute carrier family 7 (cationic amino acid transporter, y+ system), member 5" |
| 1631634 | 9q34.11 | MGC3038 | "hypothetical protein similar to actin related protein 2/3 complex, subunit 5" |
| 725454 | 9q22 | CKS2 | CDC28 protein kinase 2 |
| 825470 | 17q21-q22 | TOP2A | topoisomerase (DNA) II alpha (170 kD) |
| 796469 | 1q32.1 | HSPC150 | HSPC150 protein similar to ubiquitin-conjugating enzyme |
| 705064 | 4p16.3 | TACC3 | "transforming, acidic coiled-coil containing protein 3" |
| 471568 | 17q25 | HN1 | hematological and neurological expressed 1 |
| 742707 | 7 | ESTs, Weakly similar to MUC2_HUMAN MUCIN 2 PRECURSOR [*H. sapiens*] |
| 624667 | 9q34.13 | LOC51117 | CGI-92 protein |
| 1422338 | 2p25-p24 | RRM2 | ribonucleotide reductase M2 polypeptide |
| 700792 | 14q22 | CDKN3 | cyclin-dependent kinase inhibitor 3 (CDK2-associated dual specificity phosphatase) |
| 280375 | 8p22 | PRO2000 | PRO2000 protein |
| 122241 | 1p34.2 | PSMB2 | "proteasome (prosome, macropain) subunit, beta type, 2" |
| 2309073 | 2q33-q34 | FZD5 | frizzled (*Drosophila*) homolog 5 |
| 2322367 | 2p14-p13 | RTN4 | reticulon 4 |
| 796694 | 17q25 | BIRC5 | baculoviral IAP repeat-containing 5 (survivin) |
| 74677 | | *Homo sapiens*, Similar to RIKEN cDNA A430107J06 gene, clone MGC: 21416 IMAGE: 4452699, mRNA, complete cds |
| 824524 | 17q21.32 | UGTREL1 | UDP-galactose transporter related |
| 825282 | | DKFZP586L0724 | DKFZP586L0724 protein |
| 824962 | 17q23.1-q23.3 | KPNA2 | "karyopherin alpha 2 (RAG cohort 1, importin alpha 1)" |
| 42831 | 11q11-q12 | NTKL | N-terminal kinase-like |
| 814054 | 1q24-25 | KIAA0040 | KIAA0040 gene product |
| 2054635 | 20q13.33 | PSMA7 | "proteasome (prosome, macropain) subunit, alpha type, 7" |
| 210862 | 17q24-17q25 | ACOX1 | "acyl-Coenzyme A oxidase 1, palmitoyl" |
| 897997 | Xp11.22-p11.21 | SMC1L1 | "SMC1 (structural maintenance of chromosomes 1, yeast)-like 1" |
| 769890 | 14q13.1 | NP | nucleoside phosphorylase |
| 756595 | 1q21 | S100A10 | "S100 calcium-binding protein A10 (annexin II ligand, calpactin I, light polypeptide (p11))" |
| 951233 | 2q35 | PSMB3 | "proteasome (prosome, macropain) subunit, beta type, 3" |
| 529827 | Xp22.31 | SYAP1 | reserved |
| 1660666 | Xp21.1 | CA5B | "carbonic anhydrase VB, mitochondrial" |
| 1696757 | 13q22.2 | KIAA1165 | hypothetical protein KIAA1165 |
| 361922 | 1p34 | ZMPSTE24 | "zinc metalloproteinase, STE24 (yeast, homolog)" |
| 823598 | | PSMD12 | "proteasome (prosome, macropain) 26S subunit, non-ATPase, 12" |
| 772220 | 3q21.2 | PDIR | for protein disulfide isomerase-related |
| 703707 | 8q12.1 | ASPH | aspartate beta-hydroxylase |
| 78869 | 20q13.33 | GP110 | "cell membrane glycoprotein, 110000M(r) (surface antigen)" |
| 1474424 | 17 | *Homo sapiens* cDNA FLJ31911 fis, clone NT2RP7004751 |
| 1947647 | 17q23.3 | LOC51651 | CGI-147 protein |
| 897609 | 12q23.2 | FLJ10074 | hypothetical protein FLJ10074 |
| 753378 | 4q34.1 | FLJ22649 | hypothetical protein FLJ22649 similar to signal peptidase SPC22/23 |
| 124331 | 16 | CPSF5 | "cleavage and polyadenylation specific factor 5, 25 kD subunit" |
| 327506 | 15 | *Homo sapiens* mRNA full length insert cDNA clone EUROIMAGE 327506 |
| 345538 | 9q21-q22 | CTSL | cathepsin L |
| 753320 | 8q13.3 | FLJ20533 | hypothetical protein FLJ20533 |
| 823907 | 8q12.2 | FLJ10511 | hypothetical protein FLJ10511 |
| 149355 | 8q13.1 | TRAM | translocating chain-associating membrane protein |
| 347373 | 8q13.3 | TCEB1 | "transcription elongation factor B (SIII), polypeptide 1 (15 kD, elongin C)" |

TABLE 6-continued

| IMAGE Clone ID | Chromosomal location | Description |
|---|---|---|
| 2028949 | 17q21.31 | PRO1855 | hypothetical protein PRO1855 |
| 624627 | 2p25-p24 | RRM2 | ribonucleotide reductase M2 polypeptide |
| 731023 | 9q34 | WDR5 | WD repeat domain 5 |
| 786067 | 20p13 | CDC25B | cell division cycle 25B |
| 878330 | 3 | *Homo sapiens* cDNA: FLJ22044 fis, clone HEP09141 |
| 1631132 | 11q12.1 | PHT2 | peptide transporter 3 |
| 756442 | 7q11.2 | POR | P450 (cytochrome) oxidoreductase |
| 823930 | 7q22.1 | ARPC1A | "actin related protein 2/3 complex, subunit 1A (41 kD)" |
| 268946 | 2 | *Homo sapiens* cDNA FLJ31861 fis, clone NT2RP7001319 |
| 1914863 | 2p13.3-p13.1 | DYSF | "dysferlin, limb girdle muscular dystrophy 2B (autosomal recessive)" |
| 789012 | 3p25-p24 | FBLN2 | fibulin 2 |
| 781047 | 2q14 | BUB1 | budding uninhibited by benzimidazoles 1 (yeast homolog) |
| 753428 | 8 | *Homo sapiens*, Similar to RIKEN cDNA 1110014B07 gene, clone MGC: 20766 IMAGE: 4586039, mRNA, complete cds |

The genes of "blue bar" genes along with their I.M.A.G.E. Consortium CloneID number, chromosomal location and descriptive identifiers (if known) are listed in Table 7.

TABLE 7

| IMAGE Clone ID | Chromosomal location | Description |
|---|---|---|
| 286378 | 19q13.4 | ZNF135 | zinc finger protein 135 (clone pHZ-17) |
| 854763 | 2q31.1 | MGC20702 | hypothetical protein MGC20702 |
| 344959 | 4p16.2 | HSA250839 | gene for serine/threonine protein kinase |
| 278222 | 18 | *Homo sapiens*, clone MGC: 10083 IMAGE: 3897118, mRNA, complete cds |
| 1679977 | 18 | *Homo sapiens*, clone MGC: 10083 IMAGE: 3897118, mRNA, complete cds |
| 504959 | 11 | *Homo sapiens* mRNA; cDNA DKFZp586G0321 (from clone DKFZp586G0321) |
| 342181 | 18q21.3 | BCL2 | B-cell CLL/lymphoma 2 |
| 502988 | 19p13.3-p13.2 | ZNF20 | zinc finger protein 20 (KOX 13) |
| 590310 | 2 | *Homo sapiens*, clone MGC: 17393 IMAGE: 3914851, mRNA, complete cds |
| 186301 | 11 | *Homo sapiens* cDNA FLJ12924 fis, clone NT2RP2004709 |
| 357120 | 16 | *Homo sapiens*, clone IMAGE: 3538007, mRNA, partial cds |
| 203003 | 16p13.3 | NME4 | "non-metastatic cells 4, protein expressed in" |
| 725649 | 14q11.2 | NFATC4 | "nuclear factor of activated T-cells, cytoplasmic, calcineurin-dependent 4" |
| 2014373 | 2q11.2 | HNK-1ST | HNK-1 sulfotransferase |
| 183440 | 22q13.33 | ARSA | arylsulfatase A |
| 2014856 | 1q25.3 | HLALS | "major histocompatibility complex, class I-like sequence" |
| 256619 | 10p11.2 | HSD17B7 | hydroxysteroid (17-beta) dehydrogenase 7 |
| 768570 | 1q21.2 | FLJ11280 | hypothetical protein FLJ11280 |
| 2975668 | 11p13 | RAG2 | recombination activating gene 2 |
| 278430 | 2q23.3 | KIF5C | kinesin family member 5C |
| 1558233 | 3 | ESTs |
| 627248 | 5q23.2 | SBBI31 | SBBI31 protein |
| 1517171 | 10p15-p14 | IL2RA | "interleukin 2 receptor, alpha" |
| 1492468 | 1p32.3 | KIAA0452 | DEME-6 protein |
| 292770 | 1 | *Homo sapiens*, clone IMAGE: 3627860, mRNA, partial cds |
| 1456701 | 1q21 | BCL9 | B-cell CLL/lymphoma 9 |
| 743146 | 18p11.21 | FLJ23403 | hypothetical protein FLJ23403 |
| 1557637 | 5 | ESTs |
| 1583198 | 5 | ESTs, Weakly similar to S65824 reverse transcriptase homolog [*H. sapiens*] |
| 741891 | 6p21.3 | RAB2L | "RAB2, member RAS oncogene family-like" |
| 179572 | 1 | *Homo sapiens* cDNA FLJ14227 fis, clone NT2RP3004095 |
| 1569902 | 16p11.2 | KIAA0556 | KIAA0556 protein |
| 127646 | 18 | ESTs, Weakly similar to T00365 hypothetical protein KIAA0670 [*H. sapiens*] |
| 782688 | 1p35.1 | P28 | "dynein, axonemal, light intermediate polypeptide" |
| 1883630 | 15 | KIAA1547 | KIAA1547 protein |
| 725340 | 4p16.3 | TETRAN | tetracycline transporter-like protein |
| 726890 | 10q24.2 | MGC4643 | hypothetical protein MGC4643 |
| 82322 | 2p23.3 | RBSK | ribokinase |
| 839382 | 9 | *Homo sapiens*, Similar to RIKEN cDNA 1700017I11 gene, clone MGC: 26847 IMAGE: 4821517, mRNA, complete cds |
| 49630 | 3p14.3 | CACNA1D | "calcium channel, voltage-dependent, L type, alpha 1D subunit" |
| 32050 | 2 | *Homo sapiens* mRNA; cDNA DKFZp586P1124 (from clone DKFZp586P1124) |
| 110226 | | TNFRSF10C | "tumor necrosis factor receptor superfamily, member 10c, decoy without an intracellular domain" |
| 1932725 | 1q32.1 | ZNF281 | zinc finger protein 281 |
| 279720 | 11 | *Homo sapiens*, Similar to RIKEN cDNA 1700008D07 gene, clone MGC: 9830 IMAGE: 3863323, mRNA, complete cds |
| 1733262 | 3p21.3 | BLu | BLu protein |

TABLE 7-continued

| IMAGE Clone ID | Chromosomal location | Description |
|---|---|---|
| 197903 | 1 | ESTs, Moderately similar to unnamed protein product [*H. sapiens*] |
| 1556859 | 17 | ESTs, Weakly similar to I38022 hypothetical protein [*H. sapiens*] |
| 726699 | 16 | *Homo sapiens*, clone MGC: 9889 IMAGE: 3868330, mRNA, complete cds |

Most striking is the existence of reciprocal gradients in the intensities of these two signatures from grade I to grade III with most grade II lesions exhibiting both signatures to varying degrees (e.g., cases 130, 169, 198). Interestingly, some grade II lesions show an expression pattern that is most similar to either grade I or grade III lesions (case 41 and 43, respectively), and some grade III samples also express the grade I signature (e.g., cases 65, 88 and 112). Histological grade is an important characteristic of breast cancer with proven utility in patient prognostication and treatment (Fitzgibbons, P. L. et al.). For example, tumors of grade III are more likely to recur and are more likely to respond to chemotherapy than those of grade I (Page, D. L. et al. (2001)). However, the current tumor grading system relies mainly on histomorphological criteria, which, although highly successful in differentiating grade I from grade III tumors, are inadequate to score grade II tumors consistently (Dalton, L. W. et al.). This difficulty may be explained by the existence of a transcriptional continuum from grade I to grade III as we observed here. Therefore, a gene expression-based molecular grading system may allow greater precision in classifying breast cancer and provide greater insight into the state of progression of a particular tumor.

An expanded set of 250 genes that display increased expression in Grade I samples in comparison to Grade III samples are identified in Table 8 by use of their I.M.A.G.E. Consortium CloneID numbers along with their chromosomal location and descriptive identifiers (if known) and relative weights.

TABLE 8

| IMAGE Clone ID | Weight | Chromosome Location | Description |
|---|---|---|---|
| 344959 | 1.451333 | 4p16.2 | HSA250839 \| gene for serine/threonine protein kinase |
| 504959 | 1.28687 | 11 | *Homo sapiens* mRNA; cDNA DKFZp586G0321 (from clone DKFZp586G0321) |
| 814815 | 1.2414 | | |
| 743146 | 1.221818 | 18p11.21 | FLJ23403 \| hypothetical protein FLJ23403 |
| 417637 | 1.208243 | 4p16 | KIAA1276 \| KIAA1276 protein |
| 502988 | 1.133964 | 19p13.3-p13.2 | ZNF20 \| zinc finger protein 20 (KOX 13) |
| 1679977 | 1.131337 | 18 | *Homo sapiens*, clone MGC: 10083 IMAGE: 3897118, mRNA, complete cds |
| 342181 | 1.12098 | 18q21.3 | BCL2 \| B-cell CLL/lymphoma 2 |
| 1932725 | 1.11409 | 1q32.1 | ZNF281 \| zinc finger protein 281 |
| 70349 | 1.110469 | Xq13.1 | MLLT7 \| myeloid/lymphoid or mixed-lineage leukemia (trithorax (*Drosophila*) homolog); translocated to, 7 |
| 180561 | 1.077508 | 1p13.3 | GSTM1 \| glutathione S-transferase M1 |
| 186301 | 1.068369 | 11 | *Homo sapiens* cDNA FLJ12924 fis, clone NT2RP2004709 |
| 278222 | 1.065646 | 18 | *Homo sapiens*, clone MGC: 10083 IMAGE: 3897118, mRNA, complete cds |
| 357120 | 1.062902 | 16 | *Homo sapiens*, clone IMAGE: 3538007, mRNA, partial cds |
| 248631 | 1.04971 | 3p21.2-p21.1 | AMT \| aminomethyltransferase (glycine cleavage system protein T) |
| 43090 | 1.021857 | 20q13.12 | H-L(3)MBT \| lethal (3) malignant brain tumor l(3)mbt protein (*Drosophila*) homolog |
| 1631682 | 1.021091 | 1p32 | PPIE \| peptidylprolyl isomerase E (cyclophilin E) |
| 767176 | 1.003495 | 17p13.1 | TNFSF13 \| tumor necrosis factor (ligand) superfamily, member 13 |
| 325583 | 1.00279 | | EST |
| 1883630 | 0.979795 | 15 | KIAA1547 \| KIAA1547 protein |
| 32050 | 0.979642 | 2 | *Homo sapiens* mRNA; cDNA DKFZp586P1124 (from clone DKFZp586P1124) |
| 502518 | 0.962484 | 3p21 | LAMB2 \| laminin, beta 2 (laminin S) |
| 126415 | 0.957069 | 10 | *Homo sapiens* mRNA; cDNA DKFZp566H0124 (from clone DKFZp566H0124) |
| 82322 | 0.946458 | 2p23.3 | RBSK \| ribokinase |
| 2975668 | 0.936737 | 11p13 | RAG2 \| recombination activating gene 2 |
| 1558233 | 0.931636 | 3 | ESTs |
| 256619 | 0.928002 | 10p11.2 | HSD17B7 \| hydroxysteroid (17-beta) dehydrogenase 7 |
| 206217 | 0.92794 | 11p11.2 | NR1H3 \| nuclear receptor subfamily 1, group H, member 3 |
| 726890 | 0.926526 | 10q24.2 | MGC4643 \| hypothetical protein MGC4643 |
| 2014373 | 0.906969 | 2q11.2 | HNK-1ST \| HNK-1 sulfotransferase |
| 283124 | 0.89695 | 19 | *Homo sapiens*, clone IMAGE: 3917549, mRNA, partial cds |
| 741891 | 0.887613 | 6p21.3 | RAB2L \| RAB2, member RAS oncogene family-like |
| 49630 | 0.885374 | 3p14.3 | CACNA1D \| calcium channel, voltage-dependent, L type, alpha 1D subunit |
| 1592530 | 0.871817 | 3p21.31 | IP6K2 \| mammalian inositol hexakisphosphate kinase 2 |
| 277044 | 0.868338 | 19q13.32 | KIAA1183 \| KIAA1183 protein |
| 1566877 | 0.867336 | 11q13 | C11orf2 \| chromosome 11 open reading frame2 |
| 839796 | 0.867221 | 12p13.31 | LOC51147 \| candidate tumor suppressor p33 ING1 homolog |
| 279720 | 0.864865 | 11 | *Homo sapiens*, Similar to RIKEN cDNA 1700008D07 gene, clone MGC: 9830 IMAGE: 3863323, mRNA, complete cds |
| 511831 | 0.854961 | 3 | MGC12936 \| hypothetical protein MGC12936 |
| 2014856 | 0.849103 | 1q25.3 | HLALS \| major histocompatibility complex, class I-like sequence |
| 1652259 | 0.845966 | 7q31.3 | LKR/SDH \| lysine-ketoglutarate reductase/saccharopine dehydrogenase |
| 172783 | 0.844046 | 19 | ZNF358 \| zinc finger protein 358 |
| 267254 | 0.838823 | 17 | ESTs, Highly similar to LOX2_HUMAN ARACHIDONATE 12-LIPOXYGENASE [*H. sapiens*] |

TABLE 8-continued

| IMAGE Clone ID | Weight | Chromosome Location | Description |
|---|---|---|---|
| 725340 | 0.826253 | 4p16.3 | TETRAN | tetracycline transporter-like protein |
| 593840 | 0.82327 | 17q11.2 | DKFZP564K1964 | DKFZP564K1964 protein |
| 179572 | 0.819502 | 1 | *Homo sapiens* cDNA FLJ14227 fis, clone NT2RP3004095 |
| 854763 | 0.818371 | 2q31.1 | MGC20702 | hypothetical protein MGC20702 |
| 286378 | 0.818288 | 19q13.4 | ZNF135 | zinc finger protein 135 (clone pHZ-17) |
| 1733262 | 0.815457 | 3p21.3 | BLu | BLu protein |
| 1517171 | 0.812481 | 10p15-p14 | IL2RA | interleukin 2 receptor, alpha |
| 814826 | 0.807648 | 2 | ESTs |
| 126466 | 0.797965 | 1p34.1 | KIAA0467 | KIAA0467 protein |
| 110226 | 0.796159 | | TNFRSF10C | tumor necrosis factor receptor superfamily, member 10c, decoy without an intracellular domain |
| 344168 | 0.795755 | 10q23 | POLL | polymerase (DNA directed), lambda |
| 108667 | 0.79402 | 22q12.2 | SF3A1 | splicing factor 3a, subunit 1, 120 kD |
| 295572 | 0.792031 | 12q24.21 | KIAA0682 | KIAA0682 gene product |
| 823634 | 0.789164 | 10 | ESTs |
| 138242 | 0.787686 | 1 | ESTs, Moderately similar to MAS2_HUMAN MANNAN-BINDING LECTIN SERINE PROTEASE 2 PRECURSOR [*H. sapiens*] |
| 197903 | 0.785879 | 1 | ESTs, Moderately similar to unnamed protein product [*H. sapiens*] |
| 292770 | 0.784314 | 1 | *Homo sapiens*, clone IMAGE: 3627860, mRNA, partial cds |
| 810981 | 0.784118 | 22q13 | FLJ20699 | hypothetical protein FLJ20699 |
| 197913 | 0.777546 | 1p34.2 | SFPQ | splicing factor proline/glutamine rich (polypyrimidine tract-binding protein-associated) |
| 190059 | 0.77474 | 19p13.3 | GNG7 | guanine nucleotide binding protein (G protein), gamma 7 |
| 782688 | 0.77051 | 1p35.1 | P28 | dynein, axonemal, light intermediate polypeptide |
| 121454 | 0.76967 | 17p13.1 | ALOX12 | arachidonate 12-lipoxygenase |
| 1569902 | 0.764217 | 16p11.2 | KIAA0556 | KIAA0556 protein |
| 726699 | 0.760736 | 16 | *Homo sapiens*, clone MGC: 9889 IMAGE: 3868330, mRNA, complete cds |
| 1601845 | 0.759847 | 7q22-q31.1 | CAPRI | Ca2+-promoted Ras inactivator |
| 703964 | 0.759625 | 11q23 | INPPL1 | inositol polyphosphate phosphatase-like 1 |
| 183440 | 0.757148 | 22q13.33 | ARSA | arylsulfatase A |
| 431231 | 0.756281 | 11q13 | EFEMP2 | EGF-containing fibulin-like extracellular matrix protein 2 |
| 810358 | 0.750312 | 17p13-p11 | ACADVL | acyl-Coenzyme A dehydrogenase, very long chain |
| 1583198 | 0.749857 | 5 | ESTs, Weakly similar to S65824 reverse transcriptase homolog [*H. sapiens*] |
| 1630990 | 0.748442 | 3p21.3-p21.2 | RPL29 | ribosomal protein L29 |
| 1868349 | 0.746257 | 15q11.2-q21.3 | PLA2G4B | phospholipase A2, group IVB (cytosolic) |
| 627248 | 0.744679 | 5q23.2 | SBBI31 | SBBI31 protein |
| 127646 | 0.743672 | 18 | ESTs, Weakly similar to T00365 hypothetical protein KIAA0670 [*H. sapiens*] |
| 1635059 | 0.739062 | 9 | *Homo sapiens*, clone MGC: 16638 IMAGE: 4121964, mRNA, complete cds |
| 1456701 | 0.732349 | 1q21 | BCL9 | B-cell CLL/lymphoma 9 |
| 345764 | 0.72889 | 3p23 | SATB1 | special AT-rich sequence binding protein 1 (binds to nuclear matrix/scaffold-associating DNA's) |
| 278430 | 0.728595 | 2q23.3 | KIF5C | kinesin family member 5C |
| 1492468 | 0.72665 | 1p32.3 | KIAA0452 | DEME-6 protein |
| 590310 | 0.725531 | 2 | *Homo sapiens*, clone MGC: 17393 IMAGE: 3914851, mRNA, complete cds |
| 768570 | 0.720983 | 1q21.2 | FLJ11280 | hypothetical protein FLJ11280 |
| 1883169 | 0.716948 | 5p15.32 | FLJ20303 | hypothetical protein FLJ20303 |
| 1635062 | 0.716142 | 12q13.13 | DKFZP586A011 | DKFZP586A011 protein |
| 2757710 | 0.715294 | 10p11.2 | ZNF37A | zinc finger protein 37a (KOX 21) |
| 810741 | 0.709032 | 17p13.2 | GABARAP | GABA(A) receptor-associated protein |
| 1569077 | 0.708429 | 6 | EST |
| 1653105 | 0.708359 | 3p14-p12 | TSP50 | testes-specific protease 50 |
| 1553530 | 0.707954 | 2 | KIAA0788 | KIAA0788 protein |
| 43679 | 0.707235 | 10 | ESTs |
| 725649 | 0.706826 | 14q11.2 | NFATC4 | nuclear factor of activated T-cells, cytoplasmic, calcineurin-dependent 4 |
| 684890 | 0.705934 | 16p12.1 | FLJ20274 | hypothetical protein FLJ20274 |
| 1556859 | 0.702746 | 17 | ESTs, Weakly similar to I38022 hypothetical protein [*H. sapiens*] |
| 1557637 | 0.698307 | 5 | ESTs |
| 203003 | 0.697573 | 16p13.3 | NME4 | non-metastatic cells 4, protein expressed in |
| 46129 | 0.694321 | 12q13.1 | HDAC7A | histone deacetylase 7A |
| 839382 | 0.693177 | 9 | *Homo sapiens*, Similar to RIKEN cDNA 1700017I11 gene, clone MGC: 26847 IMAGE: 4821517, mRNA, complete cds |
| 307029 | 0.690207 | | |
| 184022 | 0.689767 | 11p15 | APBB1 | amyloid beta (A4) precursor protein-binding, family B, member 1 (Fe65) |
| 745077 | 0.681153 | 19 | *Homo sapiens* mRNA; cDNA DKFZp566J2324 (from clone DKFZp566J2324); partial cds |
| 769600 | 0.68017 | 5p15.2-p13.1 | UNG2 | uracil-DNA glycosylase 2 |
| 280776 | 0.677821 | 15 | MGC5139 | hypothetical protein MGC5139 |
| 810947 | 0.674861 | 16p13.11 | NUDE1 | LIS1-interacting protein NUDE1, rat homolog |
| 824879 | 0.674702 | 16p13.3 | MGC11275 | hypothetical protein MGC11275 |
| 454503 | 0.669502 | 12 | *Homo sapiens*, clone IMAGE: 3346451, mRNA, partial cds |
| 811920 | 0.658971 | 9p13 | IL11RA | interleukin 11 receptor, alpha |
| 1636360 | 0.658963 | 15q21.1-q21.2 | FLJ14957 | hypothetical protein FLJ14957 |
| 2502722 | 0.658146 | 11q23 | LOH11CR2A | loss of heterozygosity, 11, chromosomal region 2, gene A |
| 1609372 | 0.657294 | 14q11.2 | RIPK3 | receptor-interacting serine-threonine kinase 3 |
| 346977 | 0.655725 | 3p24.3 | KIAA0210 | KIAA0210 gene product |
| 293569 | 0.653314 | 1q25 | C1orf21 | chromosome 1 open reading frame 21 |
| 1635307 | 0.651746 | 12 | *Homo sapiens*, clone IMAGE: 3833472, mRNA |

TABLE 8-continued

| IMAGE Clone ID | Weight | Chromosome Location | Description |
|---|---|---|---|
| 240505 | 0.65172 | 14q11.2 | KIAA0323 | KIAA0323 protein |
| 52724 | 0.648958 | | FLJ20241 | hypothetical protein FLJ20241 |
| 120138 | 0.648579 | 10q21.1 | JDP1 | J domain containing protein 1 |
| 74070 | 0.648244 | 1q21.2 | ENSA | endosulfine alpha |
| 186626 | 0.644915 | 6 | ESTs, Weakly similar to CYP4_HUMAN 40 KDA PEPTIDYL-PROLYL CIS-TRANS ISOMERASE [*H. sapiens*] |
| 296679 | 0.644155 | 5 | *Homo sapiens* clone TCCCTA00151 mRNA sequence |
| 2119838 | 0.64368 | 11q25 | ADAMTS8 | a disintegrin-like and metalloprotease (reprolysin type) with thrombospondin type 1 motif, 8 |
| 813488 | 0.643211 | 1q32.1 | LOC51235 | hypothetical protein |
| 742094 | 0.639857 | 14q32.12 | FLJ20950 | hypothetical protein FLJ20950 |
| 705274 | 0.638802 | 2q37.2 | DGKD | diacylglycerol kinase, delta (130 kD) |
| 826285 | 0.633833 | | *Homo sapiens* cDNA FLJ32001 fis, clone NT2RP7009373 |
| 358217 | 0.631361 | Xq26.1 | GPC4 | glypican 4 |
| 796723 | 0.629143 | | *Homo sapiens* clone CDABP0014 mRNA sequence |
| 529843 | 0.628435 | 19 | ESTs |
| 262251 | 0.627736 | 16p13 | CLCN7 | chloride channel 7 |
| 490449 | 0.623346 | 5q31 | RAD50 | RAD50 (*S. cerevisiae*) homolog |
| 788334 | 0.622909 | 11p15.5-p15.4 | MRPL23 | mitochondrial ribosomal protein L23 |
| 1909935 | 0.62043 | 8 | ESTs |
| 250883 | 0.61921 | 3p21 | UBE1L | ubiquitin-activating enzyme E1-like |
| 1707667 | 0.618023 | 17 | *Homo sapiens* cDNA FLJ31065 fis, clone HSYRA2001142 |
| 68103 | 0.617869 | 12 | MLC1SA | myosin light chain 1 slow a |
| 773381 | 0.617263 | 19q13.33 | NAPA | N-ethylmaleimide-sensitive factor attachment protein, alpha |
| 1559596 | 0.616776 | 11 | ESTs, Highly similar to AF175283 1 zinc metalloendopeptidase [*H. sapiens*] |
| 825296 | 0.616769 | 1q42.11-q42.3 | LDLC | low density lipoprotein receptor defect C complementing |
| 866866 | 0.616211 | 3p21.3 | RASSF1 | Ras association (RalGDS/AF-6) domain family 1 |
| 490668 | 0.613699 | 3 | *Homo sapiens*, clone IMAGE: 4182947, mRNA |
| 824052 | 0.613652 | 6p21.3 | C6orf1 | chromosome 6 open reading frame 1 |
| 505243 | 0.612671 | 12p11 | ITPR2 | inositol 1,4,5-triphosphate receptor, type 2 |
| 1911343 | 0.612387 | 16p13.3 | RAB26 | RAB26, member RAS oncogene family |
| 1637296 | 0.60612 | 10q22-q23 | RPS24 | ribosomal protein S24 |
| 753252 | 0.604292 | 17q21.31 | MGC4251 | hypothetical protein MGC4251 |
| 1518890 | 0.602612 | 11q13.2-q13.3 | MTL5 | metallothionein-like 5, testis-specific (tesmin) |
| 234522 | 0.601183 | 1q21.3 | KIAA1535 | KIAA1535 protein |
| 52419 | 0.598962 | 9q13-q21 | X123 | Friedreich ataxia region gene X123 |
| 278483 | 0.598475 | 18p11.32 | TYMS | thymidylate synthetase |
| 877664 | 0.598243 | 20 | FLJ14987 | hypothetical protein FLJ14987 |
| 826622 | 0.594938 | 16p13.12 | KIAA0430 | KIAA0430 gene product |
| 701112 | 0.591773 | 3p25 | XPC | xeroderma pigmentosum, complementation group C |
| 1859625 | 0.591377 | 8q24 | BAI1 | brain-specific angiogenesis inhibitor 1 |
| 812975 | 0.586956 | 9p23 | KIAA0172 | KIAA0172 protein |
| 214068 | 0.585918 | 10p15 | GATA3 | GATA-binding protein 3 |
| 1587863 | 0.581689 | 3p23-p22 | ACAA1 | acetyl-Coenzyme A acyltransferase 1 (peroxisomal 3-oxoacyl-Coenzyme A thiolase) |
| 1518402 | 0.576275 | 17q11.1 | KIAA1361 | KIAA1361 protein |
| 796996 | 0.57565 | Xq13.1-q13.3 | IGBP1 | immunoglobulin (CD79A) binding protein 1 |
| 1323448 | 0.575218 | 7q11.23 | CRIP1 | cysteine-rich protein 1 (intestinal) |
| 2388571 | 0.574109 | 19p13.1-q12 | AKAP8 | A kinase (PRKA) anchor protein 8 |
| 75078 | 0.573276 | 12 | ESTs |
| 1604642 | 0.572299 | 6 | *Homo sapiens* cDNA FLJ32724 fis, clone TESTI2000951 |
| 66532 | 0.572179 | 20q13.2-q13.3 | EDN3 | endothelin 3 |
| 2273445 | 0.571917 | 20q11.2 | GHRH | growth hormone releasing hormone |
| 346643 | 0.567626 | 10 | ESTs |
| 595297 | 0.563887 | 1q21.3 | SNAPAP | SNARE associated protein snapin |
| 971399 | 0.561448 | 12cen-q21 | SYT1 | synaptotagmin I |
| 897550 | 0.561065 | 17q21.2 | MGC2744 | hypothetical protein MGC2744 |
| 215000 | 0.560663 | 3p22 | VIPR1 | vasoactive intestinal peptide receptor 1 |
| 155896 | 0.560564 | 11cen-q12.1 | LOC51035 | ORF |
| 1700429 | 0.56053 | 10q26 | GFRA1 | GDNF family receptor alpha 1 |
| 277463 | 0.560068 | 18p11.2 | C18orf1 | chromosome 18 open reading frame 1 |
| 1587710 | 0.556854 | 17p13.1-17p12 | PER1 | period (*Drosophila*) homolog 1 |
| 565849 | 0.55621 | 1q32.1 | C3IP1 | kelch-like protein C3IP1 |
| 126851 | 0.555748 | 10q22.1 | FLJ11160 | hypothetical protein FLJ11160 |
| 2413337 | 0.554359 | 11q23.2-q24.2 | SORL1 | sortilin-related receptor, L(DLR class) A repeats-containing |
| 824753 | 0.554027 | 13 | FLJ22624 | hypothetical protein FLJ22624 |
| 50471 | 0.553058 | 11 | *Homo sapiens* cDNA FLJ14242 fis, clone OVARC1000678 |
| 33500 | 0.552872 | | *Homo sapiens* clone 23556 mRNA sequence |
| 752547 | 0.551916 | 15 | *Homo sapiens* mRNA; cDNA DKFZp586G1520 (from clone DKFZp586G1520) |
| 83358 | 0.550166 | | ESTs |
| 2096306 | 0.55013 | 8q24.3 | ARC | activity-regulated cytoskeleton-associated protein |
| 196786 | 0.548574 | 18q23 | CYB5 | cytochrome b-5 |
| 2018808 | 0.546276 | 11q14 | PRCP | prolylcarboxypeptidase (angiotensinase C) |
| 1500542 | 0.544517 | 16p13.3 | RGS11 | regulator of G-protein signalling 11 |
| 470061 | 0.544311 | 3q25 | SIAH2 | seven in absentia (*Drosophila*) homolog 2 |
| 1762111 | 0.543871 | 5p14-p13 | NPR3 | natriuretic peptide receptor C/guanylate cyclase C (atrionatriuretic peptide receptor C) |

TABLE 8-continued

| IMAGE Clone ID | Weight | Chromosome Location | Description |
|---|---|---|---|
| 2116188 | 0.543472 | 17q21 | HDAC5 | histone deacetylase 5 |
| 826668 | 0.542351 | 6q21 | KIAA0274 | KIAA0274 gene product |
| 26736 | 0.540638 | 20 | *Homo sapiens* cDNA FLJ30872 fis, clone FEBRA2004293 |
| 669379 | 0.540325 | 7 | *Homo sapiens*, clone IMAGE: 3463399, mRNA, partial cds |
| 221776 | 0.536594 | 14 | ESTs, Weakly similar to T20410 hypothetical protein E02A10.2 - *Caenorhabditis elegans* [*C. elegans*] |
| 264632 | 0.535737 | 19 | ESTs |
| 741790 | 0.53497 | 2p13.3 | FLJ20080 | hypothetical protein FLJ20080 |
| 1626087 | 0.53252 | 3p21.31 | DKFZP434A236 | DKFZP434A236 protein |
| 812033 | 0.532407 | 2q35-q37 | GPC1 | glypican 1 |
| 950574 | 0.531092 | 17q25 | H3F3B | H3 histone, family 3B (H3.3B) |
| 284022 | 0.531011 | 8p23 | ARHGEF10 | Rho guanine nucleotide exchange factor (GEF) 10 |
| 35828 | 0.528716 | 5q23 | DTR | diphtheria toxin receptor (heparin-binding epidermal growth factor-like growth factor) |
| 2284619 | 0.528522 | 19q13.4 | ZNF132 | zinc finger protein 132 (clone pHZ-12) |
| 681992 | 0.528384 | 7 | *Homo sapiens* cDNA FLJ13384 fis, clone PLACE1001062, highly similar to *Homo sapiens* mRNA for lysine-ketoglutarate reductase/saccharopine dehydrogenase |
| 43933 | 0.52806 | Xp11.4-p11.3 | MAOA | monoamine oxidase A |
| 785538 | 0.527955 | | *Homo sapiens* cDNA FLJ32293 fis, clone PROST2001739 |
| 343760 | 0.526569 | 6q13-15 | SH3BGRL2 | SH3 domain binding glutamic acid-rich protein like 2 |
| 785571 | 0.525679 | 10 | DNAJL1 | hypothetical protein similar to mouse Dnajl1 |
| 809507 | 0.525406 | 16p13.3 | FLJ20568 | hypothetical protein FLJ20568 |
| 1895664 | 0.524227 | 15q26.1 | PRO2198 | hypothetical protein PRO2198 |
| 823661 | 0.521218 | 14 | *Homo sapiens* cDNA FLJ31768 fis, clone NT2RI2007891, moderately similar to DMR-N9 PROTEIN |
| 842980 | 0.519909 | 22q12.2 | DRG1 | developmentally regulated GTP-binding protein 1 |
| 126419 | 0.517789 | 1q21-q22 | NIT1 | nitrilase 1 |
| 1926023 | 0.516851 | 7 | ESTs, Weakly similar to T42727 proliferation potential-related protein - mouse [*M. musculus*] |
| 132857 | 0.516382 | 17 | *Homo sapiens* mRNA; cDNA DKFZp586N1323 (from clone DKFZp586N1323) |
| 855586 | 0.515352 | 5q31 | NR3C1 | nuclear receptor subfamily 3, group C, member 1 |
| 810331 | 0.515056 | 1q24 | QSCN6 | quiescin Q6 |
| 265103 | 0.512718 | 1p36 | MMEL2 | membrane metallo-endopeptidase-like 2 |
| 1521361 | 0.511233 | 8p21.2 | KIAA0717 | KIAA0717 protein |
| 432072 | 0.508774 | 18q23 | NFATC1 | nuclear factor of activated T-cells, cytoplasmic, calcineurin-dependent 1 |
| 2069602 | 0.506115 | 16q24.3 | MC1R | melanocortin 1 receptor (alpha melanocyte stimulating hormone receptor) |
| 283173 | 0.505655 | 4 | *Homo sapiens* PAC clone RP1-130H16 from 22q12.1-qter |
| 1404841 | 0.501049 | 19q13.4 | ZNF175 | zinc finger protein 175 |
| 1871116 | 0.500004 | 2 | *Homo sapiens* mRNA; cDNA DKFZp434C1714 (from clone DKFZp434C1714); partial cds |
| 758365 | 0.4988 | 12q13-q15 | OS4 | conserved gene amplified in osteosarcoma |
| 1641894 | 0.498542 | 10 | ESTs |
| 1492147 | 0.498131 | Xq13.1 | RPS4X | ribosomal protein S4, X-linked |
| 1558642 | 0.497736 | 2q37.3 | MLPH | melanophilin |
| 1641245 | 0.497723 | 18q21.1 | LOC51320 | hypothetical protein |
| 1635649 | 0.497647 | 20p13 | CDS2 | CDP-diacylglycerol synthase (phosphatidate cytidylyltransferase) 2 |
| 414999 | 0.496855 | 17q21 | ETV4 | ets variant gene 4 (E1A enhancer-binding protein, E1AF) |
| 1535957 | 0.496325 | 5p15.3 | SEC6 | similar to *S. cerevisiae* Sec6p and *R. norvegicus* rsec6 |
| 774082 | 0.495883 | 12q22-q23 | ASCL1 | achaete-scute complex (*Drosophila*) homolog-like 1 |
| 811013 | 0.494705 | 1p13.3 | AMPD2 | adenosine monophosphate deaminase 2 (isoform L) |
| 809998 | 0.493372 | 1p21 | AMY2A | amylase, alpha 2A; pancreatic |
| 2018084 | 0.48899 | 2q24.3 | SPAK | Ste-20 related kinase |
| 161373 | 0.485425 | 7q11-q22 | PMS2L4 | postmeiotic segregation increased 2-like 4 |
| 178137 | 0.485162 | 4q25 | RPL34 | ribosomal protein L34 |
| 75886 | 0.484926 | 4 | ESTs, Weakly similar to E54024 protein kinase [*H. sapiens*] |
| 429387 | 0.484053 | 7p15.3 | CHN2 | chimerin (chimaerin) 2 |
| 742977 | 0.481369 | 7p13 | DKFZP761|2123 | KIAA1886 protein |
| 240637 | 0.480946 | 1p33-p32.1 | MGC8974 | hypothetical protein MGC8974 |
| 838366 | 0.480888 | 1p36.1-p35 | HMGCL | 3-hydroxymethyl-3-methylglutaryl-Coenzyme A lyase (hydroxymethylglutaricaciduria) |
| 796181 | 0.480102 | 13q34 | GAS6 | growth arrest-specific 6 |
| 23776 | 0.479727 | 4p15.31 | QDPR | quinoid dihydropteridine reductase |
| 1909433 | 0.478064 | 17 | *Homo sapiens* cDNA FLJ30754 fis, clone FEBRA2000438 |
| 2160920 | 0.477446 | 1p13 | PHTF1 | putative homeodomain transcription factor 1 |
| 1500536 | 0.475933 | 12pter-p13.31 | MDS028 | uncharacterized hematopoietic stem/progenitor cells protein MDS028 |
| 294537 | 0.474189 | 2q37.3 | RAB17 | RAB17, member RAS oncogene family |
| 784085 | 0.469813 | 6q25-q26 | TUSP | tubby super-family protein |
| 239877 | 0.469171 | 5q31 | HDAC3 | histone deacetylase 3 |
| 626861 | 0.468844 | 11p15 | EIF4G2 | eukaryotic translation initiation factor 4 gamma, 2 |
| 741977 | 0.466816 | 6p21.3 | BF | B-factor, properdin |

Some of the genes within the tumor grade I/III signatures have been previously reported to be associated with breast cancer. Within the grade I signature, two genes, BCL2 and TNFRSF10C, are inhibitors of apoptosis. Various reports in the literature link BCL2 expression to ER-positive, low-grade tumors (van Slooten, H. J. et al.). TNFRSF10C is a decoy receptor (DcR1) for TRAIL, an apoptosis-inducing cytokine of the tumor necrosis factor (TNF) family (Sheridan, J. P. et al.). Without being bound by theory, presence of DcR1 on the surface of breast cancer cells would be expected to block signaling through the cell death receptors activated by TRAIL, thus inhibiting apoptosis.

Similarly, an expanded set of 250 genes that display increased expression in Grade III samples in comparison to Grade I samples are identified in Table 9 by use of their I.M.A.G.E. Consortium CloneID numbers along with their chromosomal location and descriptive identifiers (if known) and relative weights (which are expressed with a negative sign solely due to the relative comparison).

TABLE 9

| IMAGE Clone ID | Weight | Chromosome Location | Description |
|---|---|---|---|
| 769921 | −1.53568 | 20q13.12 | UBE2C | ubiquitin-conjugating enzyme E2C |
| 951241 | −1.33815 | 15q13.3 | ANKT | nucleolar protein ANKT |
| 1517595 | −1.3332 | 9p11.2 | KIAA0175 | likely ortholog of maternal embryonic leucine zipper kinase |
| 1474424 | −1.32072 | 17 | Homo sapiens cDNA FLJ31911 fis, clone NT2RP7004751 |
| 2309073 | −1.29533 | 2q33-q34 | FZD5 | frizzled (Drosophila) homolog 5 |
| 796469 | −1.27516 | 1q32.1 | HSPC150 | HSPC150 protein similar to ubiquitin-conjugating enzyme |
| 823598 | −1.26568 | | PSMD12 | proteasome (prosome, macropain) 26S subunit, non-ATPase, 12 |
| 700792 | −1.25232 | 14q22 | CDKN3 | cyclin-dependent kinase inhibitor 3 (CDK2-associated dual specificity phosphatase) |
| 2018131 | −1.23217 | 12p13.2-p13.1 | RACGAP1 | Rac GTPase activating protein 1 |
| 292936 | −1.20973 | 1p34.3 | FLJ10468 | hypothetical protein FLJ10468 |
| 1422338 | −1.20922 | 2p25-p24 | RRM2 | ribonucleotide reductase M2 polypeptide |
| 504308 | −1.18743 | 10cen-q26.11 | FLJ10540 | hypothetical protein FLJ10540 |
| 796694 | −1.16444 | 17q25 | BIRC5 | baculoviral IAP repeat-containing 5 (survivin) |
| 869375 | −1.15363 | 15q26.1 | IDH2 | isocitrate dehydrogenase 2 (NADP+), mitochondrial |
| 814270 | −1.14538 | 4q27 | PMSCL1 | polymyositis/scleroderma autoantigen 1 (75 kD) |
| 42831 | −1.12878 | 11q11-q12 | NTKL | N-terminal kinase-like |
| 1476053 | −1.10462 | 15q15.1 | RAD51 | RAD51 (S. cerevisiae) homolog (E coli RecA homolog) |
| 32493 | −1.10275 | 2q31.1 | ITGA6 | integrin, alpha 6 |
| 149355 | −1.10225 | 8q13.1 | TRAM | translocating chain-associating membrane protein |
| 824962 | −1.09918 | 17q23.1-q23.3 | KPNA2 | karyopherin alpha 2 (RAG cohort 1, importin alpha 1) |
| 1702742 | −1.09644 | 16q24.3 | SLC7A5 | solute carrier family 7 (cationic amino acid transporter, y+ system), member 5 |
| 824524 | −1.07854 | 17q21.32 | UGTREL1 | UDP-galactose transporter related |
| 128711 | −1.07401 | 7p15-p14 | ANLN | anillin (Drosophila Scraps homolog), actin binding protein |
| 843121 | −1.06508 | 6p22.1-p21.2 | CLIC1 | chloride intracellular channel 1 |
| 2017415 | −1.06388 | 2p24-p21 | CENPA | centromere protein A (17 kD) |
| 753378 | −1.0364 | 4q34.1 | FLJ22649 | hypothetical protein FLJ22649 similar to signal peptidase SPC22/23 |
| 825470 | −1.03507 | 17q21-q22 | TOP2A | topoisomerase (DNA) II alpha (170 kD) |
| 705064 | −1.02376 | 4p16.3 | TACC3 | transforming, acidic coiled-coil containing protein 3 |
| 2054635 | −1.02042 | 20q13.33 | PSMA7 | proteasome (prosome, macropain) subunit, alpha type, 7 |
| 781047 | −1.0153 | 2q14 | BUB1 | budding uninhibited by benzimidazoles 1 (yeast homolog) |
| 1534700 | −1.01343 | 11q21 | KIAA0830 | KIAA0830 protein |
| 1587847. | −1.01171 | 2q21 | MCM6 | minichromosome maintenance deficient (mis5, S. pombe) 6 |
| 743810 | −1.0099 | 12p13 | MGC2577 | hypothetical protein MGC2577 |
| 897609 | −0.99379 | 12q23.2 | FLJ10074 | hypothetical protein FLJ10074 |
| 66406 | −0.98421 | 2 | ESTs, Highly similar to T47163 hypothetical protein DKFZp762E1312.1 [H. sapiens] |
| 1631634 | −0.98233 | 9q34.11 | MGC3038 | hypothetical protein similar to actin related protein 2/3 complex, subunit 5 |
| 624627 | −0.96436 | 2p25-p24 | RRM2 | ribonucleotide reductase M2 polypeptide |
| 814054 | −0.95575 | 1q24-25 | KIAA0040 | KIAA0040 gene product |
| 773301 | −0.91294 | 16q22.1 | CDH3 | cadherin 3, type 1, P-cadherin (placental) |
| 1416055 | −0.91005 | 8 | KIAA0165 | extra spindle poles, S. cerevisiae, homolog of |
| 345787 | −0.89554 | 18p11.31 | HEC | highly expressed in cancer, rich in leucine heptad repeats |
| 624667 | −0.88376 | 9q34.13 | LOC51117 | CGI-92 protein |
| 786067 | −0.87714 | 20p13 | CDC25B | cell division cycle 25B |
| 785368 | −0.87699 | 8p21-p12 | TOPK | PDZ-binding kinase; T-cell originated protein kinase |
| 564981 | −0.85513 | 18 | Homo sapiens, Similar to RIKEN cDNA 2810433K01 gene, clone MGC: 10200 IMAGE: 3909951, mRNA, complete cds |
| 753320 | −0.85505 | 8q13.3 | FLJ20533 | hypothetical protein FLJ20533 |
| 529827 | −0.85016 | Xp22.31 | SYAP1 | reserved |
| 122241 | −0.84842 | 1p34.2 | PSMB2 | proteasome (prosome, macropain) subunit, beta type, 2 |
| 712139 | −0.84823 | 2q37.2 | ARL7 | ADP-ribosylation factor-like 7 |
| 259950 | −0.83947 | 8q23 | CML66 | chronic myelogenous leukemia tumor antigen 66 |
| 772220 | −0.83895 | 3q21.2 | PDIR | for protein disulfide isomerase-related |
| 124331 | −0.83664 | 16 | CPSF5 | cleavage and polyadenylation specific factor 5, 25 kD subunit |
| 842818 | −0.83338 | 16q23-q24 | KARS | lysyl-tRNA synthetase |
| 150897 | −0.82922 | 19p13.1 | B3GNT3 | UDP-GlcNAc: betaGal beta-1,3-N-acetylglucosaminyltransferase 3 |
| 823930 | −0.82876 | 7q22.1 | ARPC1A | actin related protein 2/3 complex, subunit 1A (41 kD) |
| 210862 | −0.82312 | 17q24-17q25 | ACOX1 | acyl-Coenzyme A oxidase 1, palmitoyl |
| 731023 | −0.82276 | 9q34 | WDR5 | WD repeat domain 5 |
| 665384 | −0.82232 | 16 | KIAA1609 | KIAA1609 protein |

TABLE 9-continued

| IMAGE Clone ID | Weight | Chromosome Location | Description |
|---|---|---|---|
| 815501 | −0.82108 | 19p13.3 | MGC2721 | hypothetical protein MGC2721 |
| 769890 | −0.81864 | 14q13.1 | NP | nucleoside phosphorylase |
| 209066 | −0.81121 | 20q13.2-q13.3 | STK15 | serine/threonine kinase 15 |
| 471568 | −0.81026 | 17q25 | HN1 | hematological and neurological expressed 1 |
| 725454 | −0.80701 | 9q22 | CKS2 | CDC28 protein kinase 2 |
| 951233 | −0.80178 | 2q35 | PSMB3 | proteasome (prosome, macropain) subunit, beta type, 3 |
| 268946 | −0.79976 | 2 | *Homo sapiens* cDNA FLJ31861 fis, clone NT2RP7001319 |
| 2028949 | −0.78651 | 17q21.31 | PRO1855 | hypothetical protein PRO1855 |
| 1914863 | −0.78621 | 2p13.3-p13.1 | DYSF | dysferlin, limb girdle muscular dystrophy 2B (autosomal recessive) |
| 744047 | −0.77737 | 16p12.3 | PLK | polo (*Drosophila*)-like kinase |
| 703707 | −0.77579 | 8q12.1 | ASPH | aspartate beta-hydroxylase |
| 78869 | −0.76948 | 20q13.33 | GP110 | cell membrane glycoprotein, 110000M(r) (surface antigen) |
| 742707 | −0.7686 | 7 | ESTs, Weakly similar to MUC2_HUMAN MUCIN 2 PRECURSOR [*H. sapiens*] |
| 825606 | −0.75817 | 10q24.1 | KNSL1 | kinesin-like 1 |
| 361922 | −0.7559 | 1p34 | ZMPSTE24 | zinc metalloproteinase, STE24 (yeast, homolog) |
| 756595 | −0.75094 | 1q21 | S100A10 | S100 calcium-binding protein A10 (annexin II ligand, calpactin I, light polypeptide (p11)) |
| 756442 | −0.7508 | 7q11.2 | POR | P450 (cytochrome) oxidoreductase |
| 823907 | −0.74968 | 8q12.2 | FLJ10511 | hypothetical protein FLJ10511 |
| 471196 | −0.74806 | 2q37 | ITM3 | integral membrane protein 3 |
| 753428 | −0.74668 | 8 | *Homo sapiens*, Similar to RIKEN cDNA 1110014B07 gene, clone MGC: 20766 IMAGE: 4586039, mRNA, complete cds |
| 739450 | −0.74247 | 1q21.2 | LASS2 | longevity assurance (LAG1, *S. cerevisiae*) homolog 2 |
| 1696757 | −0.73849 | 13q22.2 | KIAA1165 | hypothetical protein KIAA1165 |
| 293727 | −0.73213 | 22q13.2 | MGC861 | hypothetical protein MGC861 |
| 839682 | −0.731 | 12q22 | UBE2N | ubiquitin-conjugating enzyme E2N (homologous to yeast UBC13) |
| 1631132 | −0.73053 | 11q12.1 | PHT2 | peptide transporter 3 |
| 327506 | −0.72966 | 15 | *Homo sapiens* mRNA full length insert cDNA clone EUROIMAGE 327506 |
| 1660666 | −0.72774 | Xp21.1 | CA5B | carbonic anhydrase VB, mitochondrial |
| 280375 | −0.72588 | 8p22 | PRO2000 | PRO2000 protein |
| 796904 | −0.71939 | 6q24-q25 | PLAGL1 | pleiomorphic adenoma gene-like 1 |
| 503671 | −0.71201 | 6 | *Homo sapiens* cDNA FLJ14368 fis, clone HEMBA1001122 |
| 74677 | −0.71194 | | *Homo sapiens*, Similar to RIKEN cDNA A430107J06 gene, clone MGC: 21416 IMAGE: 4452699, mRNA, complete cds |
| 291478 | −0.71127 | 1p36 | RUNX3 | runt-related transcription factor 3 |
| 825282 | −0.7096 | | DKFZP586L0724 | DKFZP586L0724 protein |
| 878330 | −0.70859 | 3 | *Homo sapiens* cDNA: FLJ22044 fis, clone HEP09141 |
| 37671 | −0.70374 | 18q11.2 | FLJ21610 | hypothetical protein FLJ21610 |
| 789012 | −0.7019 | 3p25-p24 | FBLN2 | fibulin 2 |
| 347373 | −0.70161 | 8q13.3 | TCEB1 | transcription elongation factor B (SIII), polypeptide 1 (15 kD, elongin C) |
| 2322367 | −0.69997 | 2p14-p13 | RTN4 | reticulon 4 |
| 897997 | −0.69961 | Xp11.22-p11.21 | SMC1L1 | SMC1 (structural maintenance of chromosomes 1, yeast)-like 1 |
| 345538 | −0.69527 | 9q21-q22 | CTSL | cathepsin L |
| 1947647 | −0.69371 | 17q23.3 | LOC51651 | CGI-147 protein |
| 3172883 | −0.69164 | 11 | ESTs, Weakly similar to S24195 dopamine receptor D4 [*H. sapiens*] |
| 1035796 | −0.68832 | 1 | ESTs, Weakly similar to T33068 hypothetical protein C35E7.9 - *Caenorhabditis elegans* [*C. elegans*] |
| 746163 | −0.67918 | 8 | ESTs, Weakly similar to ALU1_HUMAN ALU SUBFAMILY J SEQUENCE CONTAMINATION WARNING ENTRY [*H. sapiens*] |
| 810711 | −0.67743 | 10q23-q24 | SCD | stearoyl-CoA desaturase (delta-9-desaturase) |
| 462926 | −0.67573 | 1q32.2-q41 | NEK2 | NIMA (never in mitosis gene a)-related kinase 2 |
| 1614140 | −0.67368 | 15q11.2-q22.33 | LOC51285 | Ris |
| 124781 | −0.66984 | 8q24.1 | SQLE | squalene epoxidase |
| 1642496 | −0.66639 | 2p24.1 | MGC11266 | hypothetical protein MGC11266 |
| 113300 | −0.66053 | 9q22.32 | TRIM14 | tripartite motif-containing 14 |
| 2014034 | −0.65845 | 2p12 | MTHFD2 | methylene tetrahydrofolate dehydrogenase (NAD+ dependent), methenyltetrahydrofolate cyclohydrolase |
| 1946448 | −0.65464 | 7q31.1 | CAV2 | caveolin 2 |
| 1635352 | −0.65164 | 4q12 | TPARL | TPA regulated locus |
| 753400 | −0.64918 | 3q27.1 | BAF53A | BAF53 |
| 1605426 | −0.64391 | 4q12 | FLJ13352 | hypothetical protein FLJ13352 |
| 565319 | −0.64374 | 8 | MAL2 | mal, T-cell differentiation protein 2 |
| 489755 | −0.64095 | 10q26.3 | ADAM12 | a disintegrin and metalloproteinase domain 12 (meltrin alpha) |
| 1916461 | −0.63993 | 22 | *Homo sapiens*, clone IMAGE: 3605655, mRNA |
| 359887 | −0.63379 | 1q32.1 | TIM17 | translocase of inner mitochondrial membrane 17 homolog A (yeast) |
| 629944 | −0.63018 | 18q12 | MYO5B | myosin VB |
| 150314 | −0.62891 | 6q13 | LYPLA1 | lysophospholipase I |
| 770355 | −0.62829 | 21q22.3 | LSS | lanosterol synthase (2,3-oxidosqualene-lanosterol cyclase) |
| 489594 | −0.6245 | Xq22.2 | FLJ11565 | hypothetical protein FLJ11565 |
| 212640 | −0.6219 | Xq28 | ARHGAP4 | Rho GTPase activating protein 4 |
| 30170 | −0.62007 | 4q34 | CASP3 | caspase 3, apoptosis-related cysteine protease |
| 51773 | −0.61957 | 7p15-p14 | MGC3077 | hypothetical protein MGC3077 |
| 490777 | −0.61906 | | |
| 1858892 | −0.61695 | Xp22.13 | MGC4825 | hypothetical protein MGC4825 |
| 358456 | −0.61552 | 7p11.2 | SEC61G | Sec61 gamma |
| 840894 | −0.61414 | 12q24.2 | COX6A1 | cytochrome c oxidase subunit VIa polypeptide 1 |

TABLE 9-continued

| IMAGE Clone ID | Weight | Chromosome Location | Description |
|---|---|---|---|
| 241348 | −0.61157 | | PCL1 | prenylcysteine lyase |
| 1505038 | −0.61123 | 8q22.2 | FLJ20171 | hypothetical protein FLJ20171 |
| 144880 | −0.60976 | 19p13.3 | LOC56932 | hypothetical protein from EUROIMAGE 1759349 |
| 454896 | −0.60575 | 16q11.1-q11.2 | DNAJA2 | DnaJ (Hsp40) homolog, subfamily A, member 2 |
| 753236 | −0.60461 | 6 | ESTs, Weakly similar to S71512 hypothetical protein T2 - mouse [*M. musculus*] |
| 266218 | −0.60106 | | |
| 418159 | −0.60025 | 22q13.1 | SYNGR1 | synaptogyrin 1 |
| 208718 | −0.59862 | 9q12-q21.2 | ANXA1 | annexin A1 |
| 781097 | −0.59718 | 11q13 | RTN3 | reticulon 3 |
| 469383 | −0.59434 | 8q21 | C8orf1 | chromosome 8 open reading frame 1 |
| 725152 | −0.59375 | 11q11 | DKFZp762A227 | hypothetical protein DKFZp762A227 |
| 845363 | −0.59313 | 17q21.3 | NME1 | non-metastatic cells 1, protein (NM23A) expressed in |
| 1460110 | −0.59206 | 14q11.2 | PSMB5 | proteasome (prosome, macropain) subunit, beta type, 5 |
| 769959 | −0.5913 | 13q34 | COL4A2 | collagen, type IV, alpha 2 |
| 796527 | −0.59108 | 7q34 | DKFZp761N0624 | hypothetical protein DKFZp761N0624 |
| 108425 | −0.59009 | 1 | ESTs, Weakly similar to JC5314 CDC28/cdc2-like kinase associating arginine-serine cyclophilin [*H. sapiens*] |
| 32231 | −0.58516 | | FLJ12442 | hypothetical protein FLJ12442 |
| 502690 | −0.58445 | 3q21.3-q25.2 | RPN1 | ribophorin I |
| 135221 | −0.58203 | 4p16 | S100P | S100 calcium-binding protein P |
| 897813 | −0.58167 | 17p11.1 | PAIP1 | polyadenylate binding protein-interacting protein 1 |
| 824352 | −0.58119 | 9q31.2 | RAD23B | RAD23 (*S. cerevisiae*) homolog B |
| 897751 | −0.58057 | 17q23 | TLK2 | tousled-like kinase 2 |
| 343607 | −0.57727 | 15q14-q24.3 | LOC55829 | AD-015 protein |
| 51899 | −0.5772 | 16q24.1 | KIAA0513 | KIAA0513 gene product |
| 726645 | −0.57716 | 16q23 | CLECSF1 | C-type (calcium dependent, carbohydrate-recognition domain) lectin, superfamily member 1 (cartilage-derived) |
| 1591264 | −0.57558 | 11p15.5-p15.4 | TALDO1 | transaldolase 1 |
| 290841 | −0.57171 | 6p21.3 | H2BFA | H2B histone family, member A |
| 486626 | −0.57063 | 8 | *Homo sapiens*, clone IMAGE: 4332938, mRNA |
| 221846 | −0.56769 | 14q24.3-q31 | CHES1 | checkpoint suppressor 1 |
| 772913 | −0.56751 | 5 | *Homo sapiens* cDNA FLJ31951 fis, clone NT2RP7007177, weakly similar to *Homo sapiens* multiple membrane spanning receptor TRC8 mRNA |
| 1686766 | −0.56178 | 6q15-q16 | RAGD | Rag D protein |
| 37708 | −0.56053 | 16q24.3 | MGC3101 | hypothetical protein MGC3101 |
| 825740 | −0.56021 | 2q32.1 | DKFZP434J1813 | DKFZP434J1813 protein |
| 741139 | −0.56009 | 20q13.1 | EYA2 | eyes absent (*Drosophila*) homolog 2 |
| 754293 | −0.55369 | 2p12 | C2orf6 | chromosome 2 open reading frame 6 |
| 83363 | −0.55322 | 6q24-q25 | PCMT1 | protein-L-isoaspartate (D-aspartate) O-methyltransferase |
| 686552 | −0.55207 | 1q42.13 | GOLPH1 | golgi phosphoprotein 1 |
| 950429 | −0.54962 | 12q | KIAA1708 | KIAA1708 protein |
| 813419 | −0.54843 | Xp11.2 | HADH2 | hydroxyacyl-Coenzyme A dehydrogenase, type II |
| 2043167 | −0.54694 | 10q25.2-q26.2 | BAG3 | BCL2-associated athanogene 3 |
| 701115 | −0.54546 | 6 | PRO2013 | hypothetical protein PRO2013 |
| 795498 | −0.54391 | 15q26.1 | HS1-2 | putative transmembrane protein |
| 965223 | −0.54333 | 17q23.2-q25.3 | TK1 | thymidine kinase 1, soluble |
| 377191 | −0.53874 | 8p22-q22.1 | LOC51123 | HSPC038 protein |
| 233679 | −0.53609 | 2p23.3 | FLJ22362 | hypothetical protein FLJ22362 |
| 590759 | −0.53571 | 4q32-q34 | SC4MOL | sterol-C4-methyl oxidase-like |
| 358083 | −0.53534 | 3q29 | KIAA0226 | KIAA0226 gene product |
| 810612 | −0.53335 | 1q21 | S100A11 | S100 calcium-binding protein A11 (calgizzarin) |
| 220395 | −0.52987 | 2p22.3 | FLJ23293 | likely ortholog of mouse ADP-ribosylation-like factor 6 interacting protein 2 |
| 280699 | −0.52812 | 7 | UCC1 | upregulated in colorectal cancer gene 1 |
| 2016775 | −0.52687 | 16p12 | GPRC5B | G protein-coupled receptor, family C, group 5, member B |
| 470124 | −0.52331 | 5p13.2 | RAD1 | RAD1 (*S. pombe*) homolog |
| 154707 | −0.51926 | 2p23-p21 | MPV17 | MpV17 transgene, murine homolog, glomerulosclerosis |
| 785933 | −0.51884 | Xp21.1 | SRPX | sushi-repeat-containing protein, X chromosome |
| 2062825 | −0.51819 | 20q11.23 | KIAA0964 | KIAA0964 protein |
| 2009491 | −0.51791 | 4q22.1-q23 | LOC51191 | cyclin-E binding protein 1 |
| 1534493 | −0.51765 | 8 | ESTs |
| 150003 | −0.5167 | 8q22.2 | FLJ13187 | phafin 2 |
| 950600 | −0.51409 | 1 | *Homo sapiens* mRNA; cDNA DKFZp586C1019 (from clone DKFZp586C1019) |
| 1455394 | −0.51333 | 7p15.2 | HCS | cytochrome c |
| 811918 | −0.51318 | 20p12.1 | KIAA0952 | KIAA0952 protein |
| 415191 | −0.51 | 2p25.3 | KIAA0161 | KIAA0161 gene product |
| 32927 | −0.50974 | 8q24.3 | FBXL6 | f-box and leucine-rich repeat protein 6 |
| 1845744 | −0.50818 | | |
| 325160 | −0.50752 | 3q13.13 | NP25 | neuronal protein |
| 812048 | −0.50542 | 20pter-p12 | PRNP | prion protein (p27-30) (Creutzfeld-Jakob disease, Gerstmann-Strausler-Scheinker syndrome, fatal familial insomnia) |
| 84161 | −0.50451 | | DKFZP434F195 | DKFZP434F195 protein |
| 897806 | −0.50236 | 14q21-q24 | HIF1A | hypoxia-inducible factor 1, alpha subunit (basic helix-loop-helix transcription factor) |
| 814378 | −0.50026 | 19q13.1 | SPINT2 | serine protease inhibitor, Kunitz type, 2 |
| 188335 | −0.49789 | | EMR2 | egf-like module containing, mucin-like, hormone receptor-like sequence 2 |

TABLE 9-continued

| IMAGE Clone ID | Weight | Chromosome Location | Description |
|---|---|---|---|
| 1585492 | −0.49501 | 9 | ESTs |
| 133213 | −0.49332 | 11q21 | FUT4 | fucosyltransferase 4 (alpha (1,3) fucosyltransferase, myeloid-specific) |
| 73009 | −0.49156 | 5 | Homo sapiens, clone MGC: 9628 IMAGE: 3913311, mRNA, complete cds |
| 785707 | −0.49031 | 15q26.1 | PRC1 | protein regulator of cytokinesis 1 |
| 84464 | −0.49025 | 1q42.12 | FLJ12806 | hypothetical protein FLJ12806 |
| 770066 | −0.48965 | 11q25 | KIAA0056 | KIAA0056 protein |
| 41208 | −0.48944 | 8p21 | BMP1 | bone morphogenetic protein 1 |
| 1698036 | −0.48904 | 20q13.2 | UBE2V1 | ubiquitin-conjugating enzyme E2 variant 1 |
| 1435862 | −0.4889 | Xp22.32 | MIC2 | antigen identified by monoclonal antibodies 12E7, F21 and O13 |
| 768452 | −0.48449 | 21 | Homo sapiens EST from clone 491476, full insert |
| 824426 | −0.48229 | 7q22.1 | PDAP1 | PDGFA associated protein 1 |
| 768561 | −0.48129 | 17q11.2-q21.1 | SCYA2 | small inducible cytokine A2 (monocyte chemotactic protein 1, homologous to mouse Sig-je) |
| 377275 | −0.48092 | 11q22-q23 | TRIM29 | tripartite motif-containing 29 |
| 470128 | −0.48 | 15q21-q22 | MYO1E | myosin IE |
| 809901 | −0.47984 | 9q21-q22 | COL15A1 | collagen, type XV, alpha 1 |
| 50772 | −0.47983 | 7p14-p13 | MGC3251 | hypothetical protein MGC3251 |
| 1843843 | −0.47902 | 12q14.1 | SRGAP1 | KIAA1304 protein |
| 823940 | −0.47897 | 17q21 | TOB1 | transducer of ERBB2, 1 |
| 564492 | −0.47749 | 11p11.12 | MTCH2 | mitochondrial carrier homolog 2 |
| 290101 | −0.47734 | X | ESTs |
| 263894 | −0.47704 | 16p12.1 | QPRT | quinolinate phosphoribosyltransferase (nicotinate-nucleotide pyrophosphorylase (carboxylating)) |
| 202901 | −0.47699 | 9q34.1 | VAV2 | vav 2 oncogene |
| 1607229 | −0.47609 | 6q22-q23 | TPD52L1 | tumor protein D52-like 1 |
| 812050 | −0.47584 | 8q24 | TRC8 | patched related protein translocated in renal cancer |
| 1637756 | −0.47545 | 1p36.3-p36.2 | ENO1 | enolase 1, (alpha) |
| 813410 | −0.47231 | 8q22.3 | POLR2K | polymerase (RNA) II (DNA directed) polypeptide K (7.0 kD) |
| 358162 | −0.47197 | 11q13.1 | HSU79266 | protein predicted by clone 23627 |
| 2062238 | −0.47184 | 2q37.1 | PSMD1 | proteasome (prosome, macropain) 26S subunit, non-ATPase, 1 |
| 753215 | −0.47119 | 7q21 | GNAI1 | guanine nucleotide binding protein (G protein), alpha inhibiting activity polypeptide 1 |
| 739126 | −0.46952 | 8q24.3 | TSTA3 | tissue specific transplantation antigen P35B |
| 1917941 | −0.46918 | 7p13 | H2AV | histone H2A.F/Z variant |
| 111362 | −0.46893 | 20q11.2 | OSBPL2 | oxysterol-binding protein-like 2 |
| 1456348 | −0.46742 | 9p24.1-p23 | SAS | N-acetylneuraminic acid phosphate synthase; sialic acid synthase |
| 263716 | −0.46636 | 21q22.3 | COL6A1 | collagen, type VI, alpha 1 |
| 810156 | −0.46594 | 2 | DTYMK | deoxythymidylate kinase (thymidylate kinase) |
| 115443 | −0.46519 | | HSPC216 | hypothetical protein |
| 32299 | −0.46427 | 18p11.2 | IMPA2 | inositol(myo)-1(or 4)-monophosphatase 2 |
| 1434897 | −0.46024 | 2q14-q32 | COL5A2 | collagen, type V, alpha 2 |
| 2028916 | −0.45905 | 10 | Homo sapiens mRNA for Hmob33 protein, 3' untranslated region |
| 2020898 | −0.45878 | 7q22 | PLOD3 | procollagen-lysine, 2-oxoglutarate 5-dioxygenase 3 |
| 487797 | −0.45837 | 1p22.1 | DR1 | down-regulator of transcription 1, TBP-binding (negative cofactor 2) |
| 284734 | −0.45795 | 6q21-q22 | WASF1 | WAS protein family, member 1 |
| 79520 | −0.45632 | 8q12.1 | RAB2 | RAB2, member RAS oncogene family |
| 812977 | −0.45368 | 12 | Homo sapiens mesenchymal stem cell protein DSC96 mRNA, partial cds |
| 810899 | −0.45368 | | ESTs |
| 428163 | −0.45286 | 3 | ESTs, Weakly similar to NAH6_HUMAN SODIUM/HYDROGEN EXCHANGER 6 [H. sapiens] |
| 613056 | −0.45261 | 11p13 | RCN1 | reticulocalbin 1, EF-hand calcium binding domain |
| 741474 | −0.45249 | 19q13.1 | GPI | glucose phosphate isomerase |
| 768989 | −0.45147 | 14 | Homo sapiens cDNA FLJ12874 fis, clone NT2RP2003769 |
| 754702 | −0.45087 | 2p25.1-p24.1 | KIAA0846 | KIAA0846 protein |
| 246800 | −0.45055 | 7p13 | FLJ10803 | hypothetical protein FLJ10803 |
| 246304 | −0.4503 | 21q21.1 | BTG3 | BTG family, member 3 |

The grade III signature contains genes known to be involved in cell cycle control (CKS2, CDC25B, MCM6), chromosomal segregation (STK15, CENPA and TACC3), and DNA recombination and repair (RAD51, UBE2N, TOP2A, RRM2). In particular, CDC25B, a potential oncogene, transforms murine diploid fibroblasts into high-grade tumors (Galaktionov, K. et al.). STK15, a centrosomal protein kinase, is frequently amplified in breast cancer, and its quantitative expression levels positively correlate with tumor grade (Zhou, H. et al. (1998b)). RAD51 has recently been shown to interact with the tumor suppressor BRCA1 (Chen, J. J., et al. (1999)), and its expression also positively correlates with tumor grade in breast cancer (Maacke, H. et al.). It has not been previously known or suspected, however, whether the expression of these genes would be capable of differentiating grade III breast cancer cells from grade I breast cancer cells. Without being bound by theory, abnormal expression of the genes associated with DNA recombination and repair and those associated with centrosomal function may result in greater genome instability, thus driving the evolution of aggressively growing and high-grade cancer cells. The data thus verified the association of several known genes with breast tumorigenesis and uncovered additional novel associations, which together may underlie the molecular basis of current tumor grading systems in breast cancer.

Figure 4:
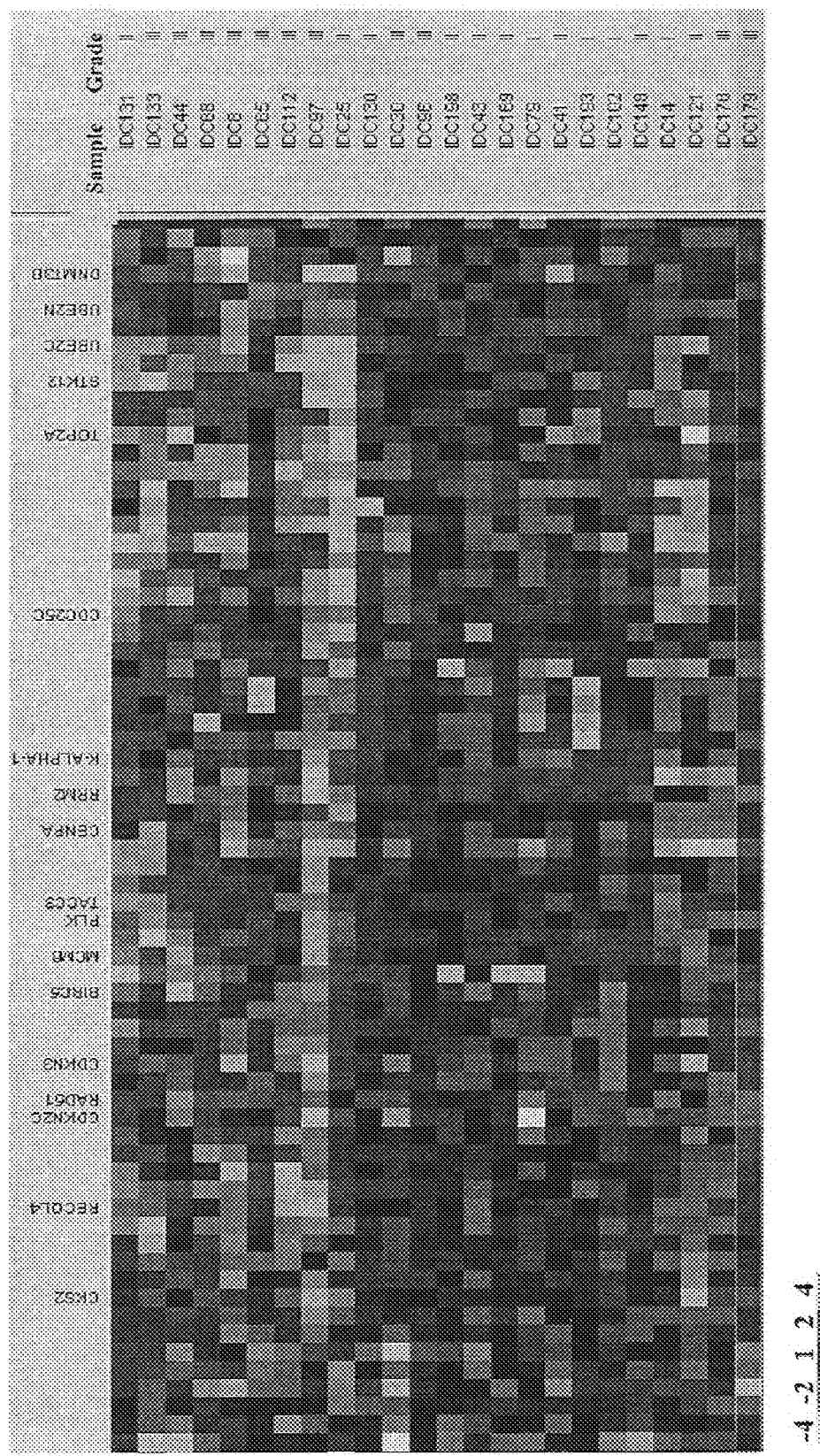
FIG. 4. Genes with increased expression in IDC relative to DCIS. Two dimensional clustering was applied to 1688 genes and 24 IDC samples and a portion of the data matrix is shown to highlight a cluster of genes with higher expression in IDC than its corresponding DCIS from the same patient. Expression values are expressed as log-ratios of expression in IDC to that in DCIS. Color scheme shown at left bottom.

The question of whether unique gene expression changes are associated with stage progression, specifically, the transition from noninvasive (DCIS) to invasive (IDC) growth, is also addressed by the present invention. The inventors have noticed that these two pathological stages are highly similar to each other with no striking differences at the level of gene expression (FIGS. 2-3). To increase our sensitivity in detecting differential gene expression between DCIS and IDC, each IDC sample was compared directly to its corresponding patient-matched DCIS sample where available. 1,688 genes showing at least a 2-fold difference between IDC and DCIS in at least 3 different sample pairs were selected and subjected to unsupervised two-dimensional hierarchical clustering. One prominent cluster of genes demonstrated elevated expression in IDC as compared with DCIS, predominately amongst the grade III IDC samples (FIG. 4). These genes, along with their I.M.A.G.E. Consortium CloneID number, along with their chromosomal location and descriptive identifiers (if known) are listed in Table 10.

TABLE 10

| IMAGE Clone ID | Chromosome Location | Description |
|---|---|---|
| 795498 | 15q26.1 | HS1-2 \| putative transmembrane protein |
| 431505 | 15q26.1 | HS1-2 \| putative transmembrane protein |
| 741139 | 20q13.1 | EYA2 \| eyes absent (*Drosophila*) homolog 2 |
| 1534592 | 2p12 | C2orf6 \| chromosome 2 open reading frame 6 |
| 290422 | 9q13-q21 | ZNF216 \| zinc finger protein 216 |
| 1609836 | 1q31 | GLUL \| glutamate-ammonia ligase (glutamine synthase) |
| 505575 | 2q35 | FLJ10116 \| hypothetical protein FLJ10116 |
| 141852 | 11q13.5-q14.1 | P2RY2 \| purinergic receptor P2Y, G-protein coupled, 2 |
| 121251 | 12q13.1 | MGC5576 \| hypothetical protein MGC5576 |
| 610326-10 | 12q12-12q14.3 | K-ALPHA-1 \| tubulin, alpha, ubiquitous |
| 725454 | 9q22 | CKS2 \| CDC28 protein kinase 2 |
| 756502 | 7p22 | NUDT1 \| nudix (nucleoside diphosphate linked moiety X)-type motif 1 |
| 504308 | 10cen-q26.11 | FLJ10540 \| hypothetical protein FLJ10540 |
| 2062329 | 6q13-q21 | TTK \| TTK protein kinase |
| 564981 | 18 | *Homo sapiens*, Similar to RIKEN cDNA 2810433K01 gene, clone MGC: 10200 IMAGE: 3909951, mRNA, complete cds |
| 951080 | 8q24.3 | RECQL4 \| RecQ protein-like 4 |
| 280375 | 8p22 | PRO2000 \| PRO2000 protein |
| 530219 | 8 | *Homo sapiens* cDNA FLJ32554 fis, clone SPLEN1000106 |
| 594438 | 1q12-1q21.2 | DJ328E19.C1.1 \| hypothetical protein |
| 470232 | 7 | ESTs, Weakly similar to I37356 epithelial microtubule-associated protein, 115K [*H. sapiens*] |
| 291057 | 1p32 | CDKN2C \| cyclin-dependent kinase inhibitor 2C (p18, inhibits CDK4) |
| 1476015 | 15q15.1 | RAD51 \| RAD51 (*S. cerevisiae*) homolog (*E coli* RecA homolog) |
| 121436 | 2q11.2 | MGC4677 \| hypothetical protein MGC4677 |
| 700792 | 14q22 | CDKN3 \| cyclin-dependent kinase inhibitor 3 (CDK2-associated dual specificity phosphatase) |
| 308633 | 10q23-q24 | HELLS \| helicase, lymphoid-specific |
| 809588 | 8q12.1 | GGH \| gamma-glutamyl hydrolase (conjugase, folylpolygammaglutamyl hydrolase) |
| 1455394 | 7p15.2 | HCS \| cytochrome c |
| 796694 | 17q25 | BIRC5 \| baculoviral IAP repeat-containing 5 (survivin) |
| 2018131 | 12p13.2-p13.1 | RACGAP1 \| Rac GTPase activating protein 1 |
| 1587847 | 2q21 | MCM6 \| minichromosome maintenance deficient (mis5, *S. pombe*) 6 |
| 743810 | 12p13 | MGC2577 \| hypothetical protein MGC2577 |
| 744047 | 16p12.3 | PLK \| polo (*Drosophila*)-like kinase |
| 705064 | 4p16.3 | TACC3 \| transforming, acidic coiled-coil containing protein 3 |
| 1518591 | | |
| 810899 | | ESTs |
| 2018976 | 5q35.1 | PTTG1 \| pituitary tumor-transforming 1 |
| 2017415 | 2p24-p21 | CENPA \| centromere protein A (17 kD) |
| 815501 | 19p13.3 | MGC2721 \| hypothetical protein MGC2721 |
| 624627 | 2p25-p24 | RRM2 \| ribonucleotide reductase M2 polypeptide |
| 1422338 | 2p25-p24 | RRM2 \| ribonucleotide reductase M2 polypeptide |
| 610326-8 | 12q12-12q14.3 | K-ALPHA-1 \| tubulin, alpha, ubiquitous |
| 79761 | 12q22 | TMPO \| thymopoietin |
| 610326-2 | 12q12-12q14.3 | K-ALPHA-1 \| tubulin, alpha, ubiquitous |
| 610326-4 | 12q12-12q14.3 | K-ALPHA-1 \| tubulin, alpha, ubiquitous |
| 610326-3 | 12q12-12q14.3 | K-ALPHA-1 \| tubulin, alpha, ubiquitous |
| 1476065 | 1p36.1-p35 | STMN1 \| stathmin 1/oncoprotein 18 |
| 293785 | 11 | ESTs, Weakly similar to A46010 X-linked retinopathy protein [*H. sapiens*] |
| 47781 | 17 | TEM7 \| tumor endothelial marker 7 precursor |
| 415102 | 5q31 | CDC25C \| cell division cycle 25C |
| 869375 | 15q26.1 | IDH2 \| isocitrate dehydrogenase 2 (NADP+), mitochondrial |
| 951241 | 15q13.3 | ANKT \| nucleolar protein ANKT |
| 814270 | 4q27 | PMSCL1 \| polymyositis/scleroderma autoantigen 1 (75 kD) |
| 785368 | 8p21-p12 | TOPK \| PDZ-binding kinase; T-cell originated protein kinase |
| 66406 | 2 | ESTs, Highly similar to T47163 hypothetical protein DKFZp762E1312.1 [*H. sapiens*] |
| 292936 | 1p34.3 | FLJ10468 \| hypothetical protein FLJ10468 |
| 1517595 | 9p11.2 | KIAA0175 \| likely ortholog of maternal embryonic leucine zipper kinase |
| 128711 | 7p15-p14 | ANLN \| anillin (*Drosophila* Scraps homolog), actin binding protein |
| 200402 | 20q11.22-q12 | DJ616B8.3 \| hypothetical protein dJ616B8.3 |
| 825470 | 17q21-q22 | TOP2A \| topoisomerase (DNA) II alpha (170 kD) |
| 769890 | 14q13.1 | NP \| nucleoside phosphorylase |
| 796469 | 1q32.1 | HSPC150 \| HSPC150 protein similar to ubiquitin-conjugating enzyme |
| 531319 | 17p13.1 | STK12 \| serine/threonine kinase 12 |
| 1416055 | 8 | KIAA0165 \| extra spindle poles, *S. cerevisiae*, homolog of |
| 769921 | 20q13.12 | UBE2C \| ubiquitin-conjugating enzyme E2C |
| 770992 | | |

TABLE 10-continued

| IMAGE Clone ID | Chromosome Location | Description |
|---|---|---|
| 839682 | 12q22 | UBE2N | ubiquitin-conjugating enzyme E2N (homologous to yeast UBC13) |
| 840364 | 20cen-q13.1 | AHCY | S-adenosylhomocysteine hydrolase |
| 276915 | 20q11.2 | DNMT3B | DNA (cytosine-5-)-methyltransferase 3 beta |

Interestingly, many of the genes in this cluster have been identified already within the grade III signature cluster (FIG. 3). These include genes involved in the cell cycle (e.g., MCM6, TOP2A, CKS2, CDC25C), centrosomal function (TACC3, CENPA), and DNA repair (RAD51, RRM2). Thus, a subset of genes that are expressed at high levels in grade III DCIS are further elevated in IDC, suggesting an intriguing link between the two lines of cancer progression, i.e., tumor grade and invasion. Indeed, and without being bound by theory, RRM2, the M2 subunit of ribonucleotide reductase (RR), which catalyzes a rate-limiting step in DNA synthesis and repair, may play a dual role in both proliferative growth and invasion; overexpression of RRM2 in human cancer cells enhances their invasive potential (Zhou, B. S. et al. (1998c)), whereas its decreased expression inhibits cancer cell proliferation (Chen, S. et al. (2000)). In addition, centrosome amplification (e.g., induced by overexpression of STK15, Zhou et al. 1998b) may result in both high tumor grade and increased invasion potential due to altered cytoskeletal architecture (Lingle, W. L. et al.). However, these genes are not associated with the transition of grade I DCIS to grade I IDC, suggesting that the latter may employ a different mechanism (s) to gain invasion potential.

Without being bound by theory, and offered for the purposes of improving the understanding of the present invention and its possible applications, the above LCM-derived gene expression profiles of the various phenotypic stages of breast cancer are consistent with a modified model of breast cancer progression (FIG. 5) In this model, breast cancer develops along two dimensions, one of which consists of stage transitions from normal to ADH to DCIS to IDC and another consists of tumor grade progression from grade I to II to III. This model is supported by existing histopathological and clinical data (see Dupont, W. D. et al.; Marshall, L. M. et al.; Betsill, W. L. et al.; and Page, D. L. et al. (1982)) and the following lines of evidence presented above. First, extensive changes in gene expression occur in ADH and persist in DCIS/IDC, suggesting a molecular linkage between ADH and DCIS/IDC. Second, the identified 200 genes whose expression levels quantitatively correlate with tumor grade progression in both DCIS and IDC indicate a transcriptional continuum from low to high-grade tumors. Finally, grade III DCIS and IDC differ quantitatively in the expression of the same genes associated with tumor grade progression. It is thus proposed that the various subtypes (e.g., ER+ and ER− subtypes) of breast cancer represent snapshots of this two-dimensional progression scheme; for example (and without limiting the invention), during the progression from grade I through grade III, ER-positive lesions evolve into ER-negative ones. The present invention thus provides the identity, and thus sequences, of various genes associated with the initiation and progression of breast cancer, and so provides for novel diagnostic, preventative and therapeutic strategies for women with breast cancer. This includes the ability to utilize the grade of DCIS/IDC breast cancer, irrespective of which stage of breast cancer is actually present, as a criterion for decisions concerning breast cancer diagnosis and treatment.

The following Table 11 summarizes the contents of Tables 2-10

TABLE 11

| Table | Description |
|---|---|
| 2 | Genes with elevated expression in ADH and persisting through DCIS and IDC cells compared to normal cells |
| 3 | Genes with highest expression in grade III DCIS or IDC cells |
| 4 | Genes with decreased expression in ADH, DCIS and IDC cells compared to normal cells |
| 5 | Genes correlated with grade I and III samples and decreased expression in all samples |
| 6 | Genes with increased expression in grade III (DCIS and/or IDC) samples |
| 7 | Genes with increased expression in grade I (DCIS and/or IDC) samples |
| 8 | 250 genes with increased expression in grade I (DCIS and/or IDC) samples |
| 9 | 250 genes with increased expression in grade III (DCIS and/or IDC) samples |
| 10 | Genes with quantitative differences in expression between DCIS and IDC samples |

Having now generally described the invention, the same will be more readily understood through reference to the following examples which are provided by way of illustration, and are not intended to be limiting of the present invention, unless specified.

EXAMPLES

Example I

Materials and Methods

Clinical specimen collection and clinicopathological parameters. All breast specimens were obtained from the Massachusetts General Hospital between 1998 and 2001. Thirty-six breast cancer patients were selected, 31 of which were diagnosed with two or more pathological stages of breast cancer progression, and 5 of which were diagnosed with pre-invasive disease only. Three healthy women who underwent elective mammoplasty reduction were selected as disease-free normal controls. Tissue specimens that demonstrated one or more pathological lesions (ADH, DCIS and IDC) were selected for the study. Cases of ADH were selected as proliferative epithelial lesions that possessed some, but not all, of the features of carcinoma in situ (Page, D. L. et al. (1992)) and most closely resemble those lesions described as CAPSS (Oyama, T. et al. and Fraser, J. L. et al.). DCIS and IDC were classified (histological grade) according to the European classification (Holland, R. et al.) and by the Nottingham combined histological grade (Elston, C. W. et al.), respectively. ER and PR expression were determined by immunohistochemical staining (negative when none of the tumor cell nuclei showed staining), and Her-2 expression determined by immunohistochemistry or FISH. This study was approved the Massachusetts General Hospital human research committee in accordance with NIH human research study guidelines.

LCM and RNA isolation and amplification. Each component (Normal, ADH, DCIS or IDC) was laser capture microdissected in triplicate (from consecutive tissue sections) as described (Sgroi et al.) using a PixCell II LCM system (Arcturus Engineering Inc., Mountain View, Calif.). Total RNA was extracted from the captured cells using the Picopure™ RNA Isolation Kit (Arcturus). T7-based RNA amplification was carried out using the RiboAmp™ kit (Arcturus). Briefly, the RNA from each sample was primed with an oligo-dT primer containing a T7 promoter sequence, reverse transcribed and then converted to double stranded cDNA. The cDNA templates were then used in an in vitro transcription reaction using T7 RNA polymerase to generate amplified RNA (aRNA). To obtain enough aRNA for a microarray experiment, a second round of RNA amplification was performed on all samples. To serve as reference in microarray hybridizations, a human universal reference RNA from Stratagene (La Jolla, Calif.) was amplified identically.

Fabrication of microarrays. Sequence-verified human cDNA clones were obtained from Research Genetics (Huntsville, Ala.). cDNA clones (from the I.M.A.G.E. Consortium via Research Genetics) inserts were amplified by PCR, gel-purified, and spotted onto a 1×3-inch SuperAmine™ (TeleChem International, Sunnyvale, Calif.) glass microscope slide using an OmniGrid™ robotic arrayer (GeneMachines, San Carlos, Calif.). As used herein, the I.M.A.G.E. Consortium CloneID, or the IMAGE CloneID, lists the identifiers of the cDNA clones on the microarrays according to the I.M.A.G.E. Consortium and Research Genetics (www.resgen.com/). This provides a unique single identifier for each clone. Descriptive names of clones (or genes) use the UniGene symbols and titles (www.ncbi.nlm.nih.gov/UniGene/).

Probe labeling and hybridization. cDNA was transcribed from aRNA in the presence of 5-(3-aminoallyl)-2'-deoxyuridine 5'-triphosphate (aminoallyl dUTP) using Stratagene's FairPlay kit™ (La Jolla, Calif.). Cy3 or Cy5 mono-reactive dye (Amersham, Piscataway, N.J.) was conjugated onto purified cDNA and the residual dye was removed using QiaQuick PCR Purification columns (Qiagen, Valencia, Calif.). Each Cy5-labeled cDNA was hybridized together with the Cy3-labeled reference probe to a microarray in 40 µL hybridizations solution (5×SSC, 0.1 µg/µL COT I, 0.2% SDS, 50% form amide) at a concentration of 25 ng/µL per channel for 17 hrs at 42° C. in >60% relative humidity.

Washing, scanning and image analysis. After hybridization, slides were washed as follows: 1×SSC, 0.2% SDS at 42° for 5 min (two times), 1×SSC, 0.2% SDS at 55° C. for 5 min, 0.1×SSC, 0.2% SDS at 55° C. for 5 min and 0.1×SSC at RT for 2 min. Washed slides were scanned using ScanArray 5000 (PerkinElmer, Billerica, Mass.), and Cy5/Cy3-signals were quantitated using ImaGene 4.2 (BioDiscovery, Los Angeles, Calif.).

Data processing. Fluorescent intensities of Cy5 and Cy3 channels on each slide were subjected to spot filtering and normalization. Spots flagged by ImaGene were excluded from further analysis. Normalization was performed using a robust nonlinear local regression method (Yang, Y. H. et al.). The normalized ratios of Cy5/Cy3 were used to represent the relative gene expression levels in the experimental samples. Measurements from replicate samples were averaged after normalization.

Cluster and discriminant analysis. Hierarchical cluster analysis was performed in GeneMaths (v1.5, Applied-Maths, Austin, Tex.) using the cosine correlation coefficient as a measure of similarity between two genes or samples and complete linkage. Linear discriminant analysis with variance was performed within GeneMaths.

Example II

Genes Showing Significant Differences in the Pair-Wise Comparisons of Normal Vs. ADH, normal Vs. DCIS and Normal Vs. IDC by Linear Discriminant Analysis 2-3 independent LCM captures were made from the same breast biopsy for each disease state (normal, ADH, DCIS or IDC), and RNA from each capture was amplified, labeled, and hybridized to 2 identical 12,000-element microarrays, resulting in from 4 to 6 data points per gene per disease state. The replicate data points were averaged to represent the expression level of each gene at each cellular state, which was further transformed as data points which are the log 2 value of the ratio of data from patient matched disease/normal samples or the log 2 value of the ratio of data from patient matched IDC/DCIS samples.

REFERENCES

DeRisi, J., et al., *Use of a cDNA microarray to analyse gene expression patterns in human cancer*, Nature Genetics, (1996) 14:457-460.

Hedenfalk, I., et al., *Gene-Expression Profiles In Heredity Breast Cancer*, The New England Journal of Medicine, (Feb. 22, 2001) 344:8:539-548.

Golub, T. R., et al., *Molecular Classification of Cancer: Class Discovery and Class Prediction by Gene Expression Monitoring*, Science, (Oct. 15, 1999) 286:531-537.

Perou, Charles M., et al., *Molecular portraits of human breast tumours*, Nature, (Aug. 17, 2000) 406:747-752.

Garber, Mitchell E., et al., *Diversity of gene expression in adenocarcinoma of the lung*, Proc. Natl. Acad. Sci. USA, (Nov. 20, 2001) 98:24:13784-13789.

Perou, Charles M., et al., *Distinctive gene expression patterns in human mammary epithelial cells and breast cancers*, Proc. Natl. Acad. Sci. USA, (August 1999) 96:9212-9217.

Sgrio, Dennis C., et al., *In Vivo Gene Expression Profile Analysis of Human Breast Cancer Progression*, Cancer Research, (Nov. 15, 1999) 59:5656-5661.

Sorlie, Therese, et al., *Gene expression patterns of breast carcinomas distinguish tumor subclasses with clinical implications*, Proc. Natl. Acad. Sci., (Sep. 11, 2001) 98:19:10869-10874.

Alizadeh, Ash A., et al., *Distinct types of diffuse large B-cell lymphoma identified by gene expression profiling*, Nature, (Feb. 3, 2000) 403:503-511.

Bittner, M., et al., *Molecular classification of cutaneous malignant melanoma by gene expression profiling*, Nature (Aug. 3, 2000) 406:536-540.

West, Mike, et al., *Predicting the clinical status of human breast cancer by using gene expression profiles*, Proc. Natl. Acad. Sci., (Sep. 25, 2001) 98:20:11462-11467.

Zhou, J. et al. A novel transcription factor, ELF5, belongs to the ELF subfamily of ETS genes and maps to human chromosome 11p13-15, a region subject to LOH and rearrangement in human carcinoma cell lines. *Oncogene* 17, 2719-32. (1998a).

Fitzgibbons, P. L. et al. Prognostic factors in breast cancer. College of American Pathologists Consensus Statement 1999. *Arch Pathol Lab Med* 124, 966-78. (2000).

Page, D. L. et al Prediction of node-negative breast cancer outcome by histologic grading and S-phase analysis by flow cytometry: an Eastern Cooperative Oncology Group Study (2192). *Am J Clin Oncol* 24, 10-8. (2001).

Dalton, L. W. et al. Histologic grading of breast cancer: linkage of patient outcome with level of pathologist agreement. *Mod Pathol* 13, 730-5. (2000).

van Slooten, H. J. et al Expression of Bcl-2 in node-negative breast cancer is associated with various prognostic factors, but does not predict response to one course of perioperative chemotherapy. *Br J Cancer* 74, 78-85. (1996).

Sheridan, J. P. et al. Control of TRAIL-induced apoptosis by a family of signaling and decoy receptors. *Science* 277, 818-21. (1997).

Galaktionov, K. et al. CDC25 phosphatases as potential human oncogenes. *Science* 269, 1575-7. (1995).

Zhou, H. et al. Tumour amplified kinase STK15/BTAK induces centrosome amplification, aneuploidy and transformation. *Nat Genet* 20, 189-93. (1998b).

Chen, J. J., Silver, D., Cantor, S., Livingston, D. M. & Scully, R. BRCA1, BRCA2, and Rad51 operate in a common DNA damage response pathway. *Cancer Res* 59, 1752s-1756s. (1999).

Maacke, H. et al. Over-expression of wild-type Rad51 correlates with histological grading of invasive ductal breast cancer. *Int J Cancer* 88, 907-13. (2000).

Zhou, B. S. et al. Overexpression of transfected human ribonucleotide reductase M2 subunit in human cancer cells enhances their invasive potential. *Clin Exp Metastasis* 16, 43-9. (1998c).

Chen, S., Zhou, B., He, F. & Yen, Y. Inhibition of human cancer cell growth by inducible expression of human ribonucleotide reductase antisense cDNA. *Antisense Nucleic Acid Drug Dev* 10, 111-6. (2000).

Lingle, W. L. et al. Centrosome amplification drives chromosomal instability in breast tumor development. *Proc Natl Acad Sci USA* 99, 1978-83. (2002).

Dupont, W. D. & Page, D. L. Risk factors for breast cancer in women with proliferative breast disease. *N Engl J Med* 312, 146-51. (1985).

Marshall, L. M. et al. Risk of breast cancer associated with atypical hyperplasia of lobular and ductal types. *Cancer Epidemiol Biomarkers Prev* 6, 297-301. (1997).

Betsill, W. L., Jr., Rosen, P. P., Lieberman, P. H. & Robbins, G. F. Intraductal carcinoma. Long-term follow-up after treatment by biopsy alone. *Jama* 239, 1863-7. (1978).

Page, D. L., Dupont, W. D., Rogers, L. W. & Landenberger, M. Intraductal carcinoma of the breast: follow-up after biopsy only. *Cancer* 49, 751-8. (1982).

Page, D. L. & Rogers, L. W. Combined histologic and cytologic criteria for the diagnosis of mammary atypical ductal hyperplasia. *Hum Pathol* 23, 1095-7. (1992).

Oyama, T., Maluf, H. & Koerner, F. Atypical cystic lobules: an early stage in the formation of low-grade ductal carcinoma in situ. *Virchows Arch* 435, 413-21. (1999).

Fraser, J. L., Raza, S., Chorny, K., Connolly, J. L. & Schnitt, S. J. Columnar alteration with prominent apical snouts and secretions: a spectrum of changes frequently present in breast biopsies performed for microcalcifications. *Am J Surg Pathol* 22, 1521-7. (1998).

Holland, R. et al. Ductal carcinoma in situ: a proposal for a new classification. *Semin Diagn Pathol* 11, 167-80. (1994).

Elston, C. W. & Ellis, I. O. Pathological prognostic factors in breast cancer. I. The value of histological grade in breast cancer: experience from a large study with long-term follow-up. *Histopathology* 19, 403-10. (1991).

Yang, Y. H. et al. Normalization for cDNA microarray data: a robust composite method addressing single and multiple slide systematic variation. *Nucleic Acids Res* 30, e15. (2002).

Unger, M. A. et al. Characterization of adjacent breast tumors using oligonucleotide microarrays. *Breast Cancer Res* 3, 336-41 (2001).

van 't Veer, L. J. et al. Gene expression profiling predicts clinical outcome of breast cancer. *Nature* 415, 530-6. (2002).

Gruvberger, S. et al. Estrogen receptor status in breast cancer is associated with remarkably distinct gene expression patterns. *Cancer Res* 61, 5979-84. (2001).

Luo, L. et al. Gene expression profiles of laser-captured adjacent neuronal subtypes. *Nat Med* 5, 117-22. (1999).

Lennon et al. The I.M.A.G.E. Consortium: An Integrated Molecular Analysis of Genomes and their Expression. *Genomics* 33:151-152 (1996).

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

We claim:

1. A method to determine the grade of breast cancer cells in a sample from a human subject, said method comprising
    assaying said sample for gene expression that is increased in grade III relative to grade I breast cancer, wherein said gene expression is assayed by synthesis of cDNA molecules from expressed RNA of the genes
    RACGAP1 (Rac GTPase activating protein 1, chromosomal location 12p13.2-p13.1),
    CENPA (centromere protein A (17kD), chromosomal location 2p24-p21),
    RRM2 (ribonucleotide reductase M2 polypeptide, chromosomal location 2p25-p24), and
    NEK2 (NIMA (never in mitosis gene a)-related kinase, chromosomal location 1q32.2-q41)
    in said sample; and
    comparing the expression of the genes, via the cDNA molecules, to the expression of said genes in reference samples of known human grade III breast cancer; and
    identifying said sample as containing grade III breast cancer cells.

2. The method of claim 1 wherein said assaying comprises preparing RNA from said sample.

3. The method of claim 2 wherein said RNA is amplified by quantitative PCR.

4. The method of claim 2 wherein said RNA is amplified by reverse transcription PCR (RT-PCR).

5. The method of claim 1 wherein said assaying comprises determining gene expression by an array.

6. The method of claim 1 wherein said sample is a ductal lavage or fine needle aspirate sample.

7. The method of claim 6 wherein said sample is microdissected to isolate one or more cells suspected of being breast cancer cells and said assaying is of RNA in said isolated cells.

8. A method to determine the grade of breast cancer cells in a sample from a human subject, said method comprising assaying said sample for gene expression that is decreased in grade I relative to grade III breast cancer, wherein said gene expression is assayed by synthesis of cDNA molecules from expressed RNA of the genes of RACGAP1 (Rac GTPase activating protein 1, chromosomal location 12p13.2-p13.1), CENPA (centromere protein A (17kD), chromosomal location 2p24-p21), RRM2 (ribonucleotide reductase M2 polypeptide, chromosomal location 2p25-p24), and NEK2 (NIMA (never in mitosis gene a)-related kinase, chromosomal location 1q32.2-q41)

in said sample; and comparing the expression of the genes, via the cDNA molecules, to the expression of said genes in reference samples of known human grade I breast cancer; and identifying said sample as containing grade I breast cancer cells.

9. The method of claim 8 wherein said assaying comprises preparing RNA from said sample.

10. The method of claim 9 wherein said RNA is amplified by quantitative PCR.

11. The method of claim 9 wherein said RNA is amplified by reverse transcription PCR (RT-PCR).

12. The method of claim 8 wherein said assaying comprises determining gene expression by an array.

13. The method of claim 8 wherein said sample is a ductal lavage or fine needle aspirate sample.

14. The method of claim 13 wherein said sample is microdissected to isolate one or more cells suspected of being breast cancer cells and said assaying is of RNA in said isolated cells.

15. The method of claim 1, wherein the assaying of said sample further includes synthesis of cDNA molecules from expressed RNA of the gene BUB1 (budding uninhibited by benzimidazoles 1 (yeast homolog), chromosomal location 2q14).

16. The method of claim 8, wherein the assaying of said sample further includes synthesis of cDNA molecules from expressed RNA of the gene BUB1 (budding uninhibited by benzimidazoles 1 (yeast homolog), chromosomal location 2q14).

17. The method of claim 15, wherein the cDNAs of said genes are synthesized by quantitative PCR of said RNAs.

18. The method of claim 15, wherein the cDNAs of said genes are synthesized by reverse transcription PCR (RT-PCR).

19. The method of claim 16, wherein the cDNAs of said genes are synthesized by quantitative PCR of said RNAs.

20. The method of claim 16, wherein the cDNAs of said genes are synthesized by reverse transcription PCR (RT-PCR).

* * * * *